US008871201B2

(12) United States Patent
Li et al.

(10) Patent No.: US 8,871,201 B2
(45) Date of Patent: Oct. 28, 2014

(54) STABILIZING FORMULATIONS

(75) Inventors: Li Li, Sudbury, MA (US); Angela Kantor, Pepperell, MA (US); Shannon B. MacMillan, Hollis, NH (US)

(73) Assignee: Wyeth LLC, New York, NY (US)

( * ) Notice: Subject to any disclaimer, the term of this patent is extended or adjusted under 35 U.S.C. 154(b) by 941 days.

(21) Appl. No.: 11/203,367

(22) Filed: Aug. 12, 2005

(65) Prior Publication Data

US 2006/0115472 A1    Jun. 1, 2006

Related U.S. Application Data

(60) Provisional application No. 60/601,311, filed on Aug. 13, 2004.

(51) Int. Cl.
| *A61K 39/395* | (2006.01) |
| *C07K 16/06* | (2006.01) |
| *C07K 16/28* | (2006.01) |
| *A61K 9/28* | (2006.01) |
| *C07K 16/30* | (2006.01) |
| *A61K 39/00* | (2006.01) |

(52) U.S. Cl.
CPC ............ *A61K 9/2886* (2013.01); *C07K 16/065* (2013.01); *C07K 16/2803* (2013.01); *C07K 16/2896* (2013.01); *C07K 16/30* (2013.01); C07K 2317/24 (2013.01)
USPC .................... 424/130.1; 424/133.1; 424/134.1

(58) Field of Classification Search
None
See application file for complete search history.

(56) References Cited

U.S. PATENT DOCUMENTS

| 4,485,110 | A | 11/1984 | Osborne et al. |
| 5,869,053 | A | 2/1999 | Stern et al. |
| 6,267,958 | B1 | 7/2001 | Andya et al. |
| 6,306,393 | B1 * | 10/2001 | Goldenberg ............... 424/141.1 |
| 6,875,432 | B2 * | 4/2005 | Liu et al. ................... 424/130.1 |
| 2002/0045571 | A1 * | 4/2002 | Liu et al. .......................... 514/2 |
| 2003/0018004 | A1 | 1/2003 | Kingsman et al. |
| 2004/0082764 | A1 | 4/2004 | Kunz et al. |
| 2004/0170623 | A1 * | 9/2004 | Arvinte et al. .............. 424/131.1 |
| 2004/0192900 | A1 | 9/2004 | Kunz et al. |
| 2005/0032216 | A1 | 2/2005 | Kingsman et al. |
| 2006/0182740 | A1 * | 8/2006 | Yang et al. ................. 424/133.1 |

FOREIGN PATENT DOCUMENTS

| CA | 2272245 | | 5/1998 |
| EP | 1 254 666 A1 | | 11/2002 |
| EP | 1 314 437 A1 | | 5/2003 |
| SE | WO 99/37329 | * | 7/1999 |
| WO | WO-87/00525 | | 1/1987 |
| WO | WO-98/56418 | | 12/1998 |
| WO | WO-99/37329 | | 7/1999 |
| WO | WO 2004/001007 A2 | | 12/2003 |
| WO | WO-2004/016286 | | 2/2004 |
| WO | WO 2005/019271 | | 3/2005 |
| WO | WO 2005/019271 A1 | | 3/2005 |
| WO | WO 2006/031653 A2 | | 3/2006 |

OTHER PUBLICATIONS

Daugherty et al. Advanced Drug Delivery Review 2006, 58:686-706.*
Human IgG purified Immunoglobulin product sheet.*
International Search Report dated Dec. 1, 2006 that issued in PCT/US05/28861.
Wang, "Instability, Stabilization, and Formulations of Liquid Protein Pharmaceuticals", International Journal of Pharmaceutics, 185:129-188 (1999).
Australian Written Opinion and Search Report issued for related Singapore Patent Application No. SG200700350-2, dated Mar. 26, 2008, as relied upon by the Intellectual Property office of Singapore.
Takahashi, et al., "The Efficacy of Anti-AFP Antibody/Adriamycin Composite Drug Against AFP-Producing Liver Tumors", Gan no Rinshou, vol. 34, No. 7 (1988)—English Translation.
Chilean Search Report issued for CL 2086-2005, dated Mar. 17, 2008.
*European Medicines Agency:* "Erbitux" Internet Citation, (2009) pp. 1-3.
*European Medicines Agency:* "Scientific discussion for the approval of Erbitux" Internet Citation (2004) pp. 1-47.
Daugherty et al., "Formulation and delivery issues for monoclonal antibody therapeutics" *Advanced Drug Delivery Reviews* (2006) vol. 58, pp. 686-706.
U.S. Appl. No. 10/016,686, filed Nov. 2, 2001, Kingsman et al.
Conry et al., J. Immunother. Emphas. Tumor Immunol., (1995), pp. 231-241, vol. 18.
Deguchi et al., J. Urol., (1987), pp. 353-358, vol. 137, No. 2.
Dias et al., Biconjugate Chem., (2005), pp. 949-958, vol. 16.
Ghetie et al., Cancer Research, (1991), pp. 5876, vol. 51.
Guillemard et al., Cancer Research, pp. 694-699, vol. 61, 2001.
Hurwitz et al., Ann. N.Y. Acad. Sci., (1983), pp. 125-136, vol. 417.
Karube et al., Nuclear Med. Biol., (1996), pp. 753-759, vol. 23.
Lee et al., Cancer Research, (2001), pp. 4474-4482, No. 61.
Lu et al., J. Pharm. Sci., (2005), pp. 788-797, vol. 94, No. 4.
Mandel et al., J. Cell Physiol., (1991), pp. 60-65, vol. 149, No. 1.
Mansfield et al., Bioconjug. Chem., (1996), pp. 557, vol. 7.
Mansfield et al., Blood, (1997), pp. 2020-2026, vol. 90.
Mishra et al., J. Drug Target, (2004), pp. 559-567, vol. 12, Nos. 9-10.
Ngai et al., Nucl. Med. Biol., (1995), pp. 77-86, vol. 22, No. 1.
Ryser et al., J. Cell Physiol., (1988), pp. 277-284, vol. 135, No. 2.
Shih et al., Cancer Immunol. Immunother., (1994), pp. 92-98, vol. 38, No. 2.
Shih et al., Cancer Research, (1991), pp. 4192-4198, vol. 51, No. 16.
Shouval et al., PNAS USA, (1988), pp. 8276-8280, vol. 85.
Smith, Seattle Genetics Curr. Opin. Investig. Drugs, (200 ), pp. 1314-1319, vol. 2, No. 9.
Stan et al., Cancer Research, (1999), pp. 115-121, vol. 59.
Takahashi et al., Gan No Rinsho, (1988), pp. 847-850, vol. 34.
Takahashi et al., Anticancer Drugs, (1996), pp. 687-696, vol. 7, No. 6.
Tassone et al., Cancer Research, (2004), pp. 4629-4636, vol. 64.
Tolcher et al., J. Clin. Oncol., (2003), pp. 211-222, vol. 21, No. 2.
Trail et al., Science, (1993), pp. 212-215, vol. 261.

* cited by examiner

*Primary Examiner* — Yunsoo Kim
(74) *Attorney, Agent, or Firm* — Fariba Shoarinejad

(57) ABSTRACT

Formulations are described that are suitable for storage of proteins, such as antibodies, over a relatively broad range of protein concentrations, pH, and buffer types. Also described are methods of storing a protein and methods of identifying a suitable formulation for storage of a specific protein. In general, a formulation contains low to no surfactant, no to relatively low salt concentrations, and requires a relatively low buffer concentration.

17 Claims, 33 Drawing Sheets

Buffers:
pH6: 50 mM succinate
pH7: 50 mM succinate 50 mM HEPES

- Fast freeze/Fast thaw
- Fast freeze/Slow thaw
- Slow freeze/Fast thaw
- Slow freeze/Slow thaw Buffer:
10 mM Na citrate, pH 5.5

Buffers:
S: 20 mM Succinate, pH6.0
SM: 20 mM Succinate, 10 mM Methionine, pH6.0
ST: 20 mM Succinate, 0.01% polysobate 80, pH6.0
SMT: 20 mM Succinate, 10 mM Methionine, 0.01% polysobate 80, pH6.0

STABILIZING FORMULATIONS

CROSS-REFERENCE TO RELATED APPLICATIONS

This application claims priority to provisional U.S. application Ser. No. 60/601311, filed on Aug. 13, 2004, which is herein incorporated by reference in its entirety.

TECHNICAL FIELD

This application relates to the field of formulation of proteins, and more particularly to the formulation of antibodies.

BACKGROUND

Proteins, such as antibodies, are often generated and stored for later use. It is important that such proteins be stored under conditions that preserve the stability of the protein under various conditions including temperature and protein concentration. Thus, formulations used for storage of proteins generally contain a variety of stabilizing substances. However, such substances can adversely affect downstream uses of the stored protein, either by reducing the efficiency of a downstream process or by necessitating the removal of one or more stabilizing substances before the protein can be used in a downstream process.

There is a need for formulations of proteins, such as antibodies, that are stable over a variety of temperatures and do not contain substances that can interfere with downstream processes using the proteins.

SUMMARY

The invention relates to the finding that certain formulations can be used for storing polypeptides such as proteins (e.g., antibodies and fragments thereof) to form a preparation that is relatively stable and simple. Such formulations reduce the likelihood that downstream processing or activity of the protein will be adversely affected by a component of the formulation and simplify the preparation of protein samples for short-term or long-term storage.

Accordingly, the invention includes a formulation that contains an isolated protein and an aqueous solution having pH 4.0-8.0, such that the formulation does not contain a cryoprotectant or surfactant, and the protein is stable for at least 3 weeks at −80° to 8° C. In some cases the formulation contains less that 150 mM salt, e.g., 75 mM salt. The protein can be an antibody (a polyclonal antibody or a monoclonal antibody). For example, the protein can be an anti-CD22 antibody, an anti-Lewis Y antibody or an anti-5T4 antibody. The protein can be a recombinant protein (e.g., a humanized monoclonal antibody). In some cases, the protein is a therapeutic protein.

The aqueous solution of the formulation can be water (e.g., filtered or sterile) or can include a buffer such as an acetate buffer, succinate buffer, phosphate buffer, or citrate buffer. In general, the buffer concentration is about 0 mM to about 150 mM, e.g., about 50 mM, about 100 mM, or about 1 mM to about 50 mM.

The protein component of the formulation is generally stable for at least 1 year at 5° C., e.g., the protein is stable for at least 3 years at 5° C. In some embodiments, the protein is present at a concentration of from about 1 mg/ml to about 200 mg/ml, about 1 mg/ml to about 100 mg/ml, about 20 mg/ml to about 200 mg/ml, about 20 mg/ml to about 100 mg/ml, about 10 mg/ml to about 30 mg/ml, 25 mg/ml to about 30 mg/ml, about 10 mg/ml to about 50 mg/ml, or about 20 mg/ml to about 50 mg/ml. The protein can have a pI of at least 6.0, e.g., at least 7.0, or at least 8.0. The protein can be purified, e.g., to at least 90% or at least 95%.

In some cases, the formulation is stored at about 0° C. to about 8° C. or from about 0° C. to about 5° C. The pH of the formulation can be about 5.0 to about 6.0, and in some cases, the pH of the formulation is about 5.0 to about 6.0 and the formulation is stored at from about −80° C. to about 5° C. Generally, the formulation is sterile.

In an example of the invention, the protein of the formulation can also be, e.g., a humanized anti-CD22 antibody and aqueous solution about 20 mM succinate, pH 6.0. In another example of the invention, the protein is an anti-Lewis Y antibody and the aqueous solution is about 10 mM Na citrate, pH 5.5 and about 75 mM NaCl. In a third example of the invention, the protein is an anti-5T4 antibody and the aqueous solution is about 10 mM Na acetate, pH about 5.5.

Stability of the formulation can be determined, e.g., by assaying at least one of, the percentage of high molecular weight species, the percentage of low molecular weight species, or the percentage of acidic species, e.g., compared to a control.

In another aspect, the invention relates to a method of storing a protein. The method includes providing a formulation as described supra, placing the formulation at a selected temperature, and maintaining the formulation at the temperature (e.g., frozen), such that the protein in the formulation is stable for at least one week, e.g., for at least one month, three months, one year, five years, seven years, or ten years. In some cases, the protein is stored and stable at a temperature of about 2° C. to 8° C. In certain embodiments, the protein is stored at a temperature of about −80° C. and the protein is stable for at least five years, seven years, or ten years. When the protein is frozen, the method can include a step in which the protein is rapidly thawed. When the protein is to be frozen, e.g., for storage, the protein can be frozen using fast freezing. In some cases, slow freezing is used. The protein can be an antibody (a monoclonal antibody or a polyclonal antibody). In one example, the protein is a humanized anti-CD22 antibody, an anti-Lewis Y antibody, or an anti-5T4 antibody. In certain embodiments, the antibody is an intermediate substance. In general, the protein is present in a concentration of at least 1 mg/ml, at least 10 mg/ml, at least 15 mg/ml, at least 20 mg/ml, or at least 30 mg/ml. Upon recovery from storage, the protein can have, e.g., at least 70% of the activity of a reference. In some cases, upon recovery from storage, the formulation contains less than or equal to 5% high molecular weight products compared to a control or upon recovery from storage, the formulation contains less than or equal to 10% high molecular weight products and aggregates, e.g., compared to a control. In some embodiments, the formulation contains less than or equal to 10% high molecular weight products, e.g., less than or equal to 5% high molecular weight products.

In another aspect, the invention relates to a method of determining a favorable formulation for storing a selected isolated protein. The method includes providing a selected isolated protein, storing the selected isolated protein in a series of formulations comprising an aqueous solution between pH 4.0 and pH 8.0 and comprising between about 0 mM to about 150 mM buffer, determining at least one parameter of stability, and identifying a formulation in which the protein is stable, such that a formulation in which the protein is stable is a favorable formulation for storing the isolated selected protein. In some embodiments of the method, a decrease in stability is indicated by at least one of an increase in the amount of high molecular weight protein in the sample, e.g., compared to a control, an increase in the amount of low molecular weight species in the sample, e.g., compared to a control, or an increase in the percent of acidic species compared to a control. In some cases, a condition is selected in which not more than 0.5%, 0.2%, or 0.1% of the protein is an high molecular weight species. The parameter of stability can be activity assayed by enzyme-linked immunoassay (ELISA) and in a stable formulation, the activity is at least 50% of a control or is at least 80% of a control. In an example of the method, the parameter of stability is the presence of high molecular weight species and a stable formulation contains not more than 5% high molecular weight species. In another example, the parameter of stability is the presence of high molecular weight species and protein aggregates, and a stable formulation includes not more than 10% high molecular weight species and protein aggregates or not more than 15% high molecular weight species and protein aggregates combined. In some cases, the percentage of high molecular weight species is compared to the amount present in a control sample (e.g., a sample before storage. In yet another embodiment of the method, the parameter of stability is the ratio of acidic and basic proteins, and the ratio in a stable formulation is not more than 15% different from a control.

The invention also relates to a polypeptide (a protein or a peptide) produced by a method that includes storage of the polypeptide in a formulation that includes an aqueous solution having a pH of 4.0 to pH 8.0, such that the formulation does not contain a cryoprotectant of surfactant, and the protein is stable for at least three weeks at −80° C. to 8° C.

In some embodiments, the polypeptide is an antibody or a fragment thereof (e.g., an anti-CD22, and anti-Lewis Y, or an anti-5T4). The antibody or fragment thereof can be conjugated to a molecule or can be used for conjugation to a molecule, for example, conjugation to a toxin such as ricin or calicheamicin.

In some embodiments, the invention relates to a polypeptide (a protein or a peptide) for use in manufacturing a modified protein, such that the polypeptide is stored in a formulation that includes an aqueous solution having a pH of 4.0 to pH 8.0, the formulation does not contain a cryoprotectant of surfactant, and the protein is stable for at least three weeks at −80° C. to 8° C. In some cases, the polypeptide is an antibody, e.g., an anti-CD22, an anti-Lewis Y, or an anti-5T4. The polypeptide can be used for manufacturing a conjugated protein, e.g., for conjugation to a toxin such as ricin or calicheamicin. Such conjugated proteins can also be stored in a formulation described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Figure 1A:
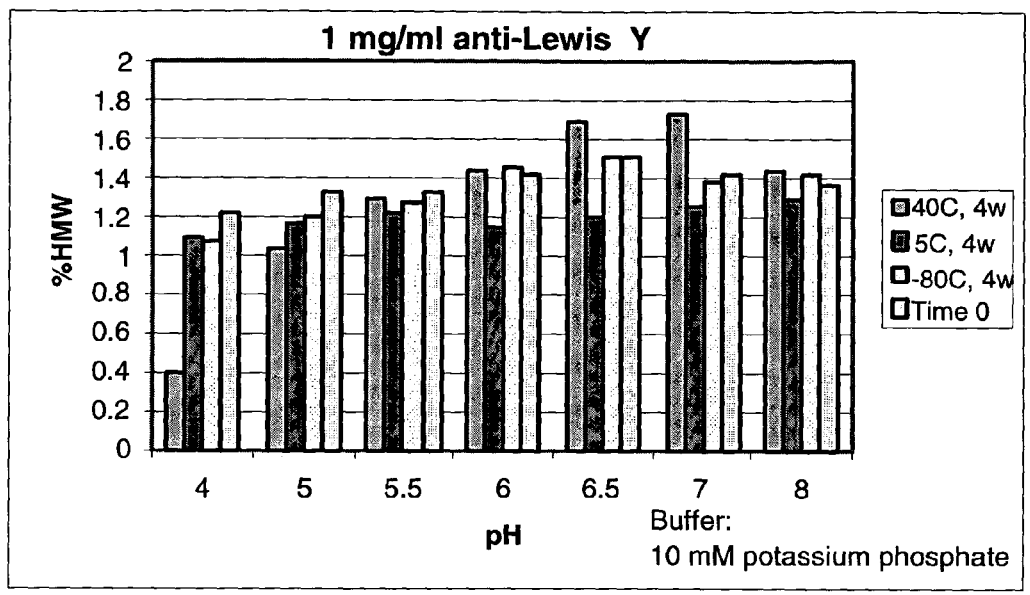
FIG. 1A is a bar graph depicting the results of size exclusion chromatography-high performance liquid chromatography (SEC-HPLC) analysis of 1 mg/ml anti-Lewis Y at various pHs and various temperatures. Results are expressed as percent high molecular weight (HMW) species.

A relatively simple formulation is provided for storage of a protein such as a monoclonal antibody, a monoclonal antibody-containing drug, or an intermediate substance in production of a protein product such as an antibody-containing drug. The formulation generally contains low to no surfactant, no to relatively low salt concentrations, and requires a relatively low buffer concentration. The formulation is effective for stable storage of certain proteins, such as antibodies, over a relatively broad range of protein concentrations, pH, and buffer types. Such formulations provide great flexibility for further processing, e.g., making the protein readily adjustable to a desired pH, excipient addition, chemical modification, or lyophilization. The formulations can also be used for storage of peptides and processed proteins, e.g., proteins such as antibodies that are conjugated to other peptide or non-peptide moieties.

Specific non-limiting examples are also provided illustrating methods of identifying a favorable formulation for storage of three different antibodies, an anti-CD22, an anti-Lewis Y, and an anti-5T4, which can be used, e.g., as intermediate substances for the manufacture of drugs made by conjugating the antibodies to a compound such as a cytotoxin. An intermediate substance is a substance, generally a protein (e.g., an antibody) that is used in the manufacture of a compound such as a drug.

Formulations

The formulations described herein generally include an isolated protein in an aqueous solution of about pH 3.0-9.0, e.g., about pH 4.0-8.0, about pH 5.0-6.5, or about pH 5.5-6.0. The formulations do not contain cryoprotectants or surfactants. In general, the formulations do not contain a preservative.

A formulation as described herein does not contain cryoprotectant. Cryoprotectants are known to those in the art, and include, for example, monosaccharides (e.g., glucose, fructose, maltose, ribose, mannose, and xylose); disaccharides (e.g., trehalose, sucrose, cellobiose, and lactose); trisaccharides (e.g., raffinose); sugar alcohols (e.g., mannitol, sorbitol, myo-inositol, phosphorylated inositols, and glycerol); polysaccharides (e.g., hydroxyethyl starch (HES), dextran, phosphorylated dextran, heparin, heparin sulphate, hyaluronic acid, dermatan sulphate, chondroitin sulphate, and agarose); carboxylic acids (e.g., pyruvate and 2,3,-diphosphoglycerate); and proteins or protein mixtures used for a protectant effect (e.g., blood, animal serum, plasma, human albumin, bovine albumin, bovine gelatin, and fish gelatin).

The new formulations do not contain a surfactant (a reagent that can reduce the surface tension of water when used in very low concentrations). Surfactants are known in the art and include, e.g., polysorbate 80, polysorbate 20, and Pluronic® surfactants.

In general, the new formulations do not contain a preservative. Preservatives are known to those in the art and include antibacterial and antifungal agents such as for example, sodium azide, mercury-containing compounds such as thimerosal, xylenols, antibiotics, isothiazolones, and amphotericin.

Buffers

Formulations can be in a buffer, meaning an agent that maintains the pH of a solution in an acceptable range. A buffer can include, for example, citrate, acetate, histidine, gluconate, succinate, phosphate, Tris (tris (hydroxymethylaminomethane)), diethanolamine, HEPES, or other organic acid buffers. Other buffers suitable for use with a protein are known to those in the art. Certain formulations exclude the use of amine buffers. In formulations containing a buffer, the buffer is generally present in a concentration ranging from greater than 0 mM to 150 mM. In some cases the buffer concentration is from about 50 mM to about 100 mM or from about 1 mM to about 50 mM. For example the buffer concentration can be from about 10 mM to 20 mM. In some cases, a combination of buffers can be used, for example, HEPES and Tris buffers can be used in combination.

Other considerations can be applied to selecting a buffer. For example, amine buffers such as Tris or histidine buffers are not suitable for certain conjugation procedures and so are not suitable for a formulation containing a protein that will be used in such a conjugation procedure.

In general, the concentration of salt used in a formulation is expressed as added salt and do not take into account, e.g., sodium contributed by buffer or salt that was present in the protein sample prior to dilution into the formulation.

Formulations can be prepared using methods known in the art. For example, dialysis can be used to introduce a buffer of the desired pH and, optionally, a salt to a formulation containing the protein of interest. Generally, an initial sample is provided that contains an isolated protein of interest. In some cases, such as when the initial sample is at a high protein concentration prior to dilution into the formulation, it is not necessary to take into account the pH or amount of salt of the initial sample. When preparing a formulation using an initial sample containing very high salt concentrations or high buffer concentrations, a method of preparing the protein is generally used that removes or reduces non-protein components of the initial sample (e.g., dialysis).

Stability

It is a feature of the formulations described herein that the protein (e.g., antibody) component of the formulation is stable for at least a specified period of time that is not less than three weeks when the formulation is stored at from −80° C. to 8° C. In general, a protein component in a formulation is stable for at least one year at 5° C. Stability generally refers to a protein's conformational stability and/or stability of activity. With respect to a formulation, a protein is stable if it meets at least one of the parameters for stability that are provided herein. In general, it is desirable to minimize the formation of high molecular weight species that accumulate during storage of a protein. Thus, one parameter for stability is that the increase, if any, in the amount of high molecular weight species in a formulation subjected to storage is less than in a control. For example, the percentage of high molecular weight species in a sample after storage in a formulation does not increase significantly compared to a control. In general, a control is a replica of the formulation that has not been subjected to storage under the experimental conditions (e.g., for three weeks at −80° to 8° C.). In some cases, the percentage of the protein component of a formulation in high molecular weight species after storage is 10% or less of the total protein, 5% or less of the total protein, is 3% or less of the total protein, or is 2% or less of the total protein. Methods of assaying high molecular weight species are known in the art and include SEC-HPLC, SDS-PAGE, capillary electrophoresis, and size exclusion chromatography Another parameter that can be assayed is the increase, if any, in the amount of low molecular weight species in a formulation subjected to storage. In general, it is desirable to minimize the accumulation of low molecular weight species during storage. For example, the percentage of low molecular weight species in a sample after storage in a formulation does not increase significantly compared to a control. In some cases, the percentage of the protein component of a formulation in high molecular weight species after storage is 10% or less of the total protein, 5% or less of the total protein, is 3% or less of the total protein, or is 2% or less of the total protein. Low molecular weight species can be assayed using methods known in the art, e.g., SEC-HPLC.

The ratio of acidic and basic species in a formulation after storage under various conditions can be compared to the ratio in a control. In general, the percentage of acidic species, indicative of deamidation, is determined. An increase in the percentage of acidic species is indicative of decreased stability. For example, a stable formulation generally displays not more than a 10% increase in the percentage of acidic species compared to a control under a selected condition. Methods of determining the percentage of acidic species in a sample are known in the art, e.g., CEX-HPLC. In some cases, the presence of basic species is assayed using methods known in the art. A change in the percentage or type of basic species present in a protein stored in a formulation is indicative of the degree of stability of the protein species in the formulation.

Another parameter for stability can be an increase in aggregates and HMW species, if any, that is less than or equal to 10% of the amount of aggregates and high molecular weight species in a control. Aggregates are generally those materials in a sample that do not enter a gel, column, or other separation medium that can be used to separate protein components of a formulation. Methods of determining high molecular weight species plus aggregates in a formulation are known in the art and include polyacrylamide gel electrophoresis, size exclusion chromatography, capillary electrophoresis, and light scattering.

The potency or activity of a protein can be determined and used as a parameter for establishing the stability of a formulation. In the case of an antibody, an immunoassay can be used (e.g., an enzyme-linked immunosorbent assay (ELISA)). When an immunoassay or other assay of activity is used, an antibody in a formulation is stable if it retains at least 50% of its activity in the immunoassay compared to the activity of a control. In some cases, the formulation is stable if the protein retains at least 20% of its activity.

Other parameters of stability can also be measured and used to evaluate a formulation. For example, the stability of a protein in a formulation after agitation (shaking) can be assayed. This can be an important parameter since it is desirable that samples remain stable during transport. Stability of a formulation with respect to agitation is generally assayed by subjecting the sample to shaking (e.g., 360 rpm) for a period of time (e.g., 12 hours, 24 hours, 48 hours, or longer) then determining whether there is an increase in products indicative of instability (e.g., high molecular weight species, low molecular weight species, or acidic species) relative to a control.

Other methods known in the art can be used to assess the stability of a protein in a formulation. Examples of such methods include circular dichroism, which provides both secondary and tertiary structural information, fluorescence spectroscopy (e.g., in the presence of Bis-ANS, which binds to hydrophobic patches as an indication of unfolding), differential scanning calorimetry (DSC, which monitors overall thermal unfolding), and ultrafiltration/diafiltration.

More than one parameter can be used to assess the stability of a protein.

Temperature

It is an advantage of certain formulations described herein that they provide a method of storing a protein in a minimal solution such that the protein does not display significant degradation or aggregation over time and over a range of temperatures. In general, a protein or peptide in the formulation is stable for at least three days (e.g., two weeks or four weeks) at temperatures ranging from about −80° C. to about 40° C. or from about −80° C. to about 8° C. (e.g., to about 5° C.). In some cases, it is desirable that a formulation be stable for extended periods of time, e.g., for at least 2 months, three months, six months, nine months, one year, three years, five years, seven years, or ten years.

In addition, a protein included in a formulation can display significant stability over repeated freeze-thaw cycles, and following such treatment can remain stable after being thawed. In general, a formulation to be frozen is quick frozen, for example, frozen in liquid nitrogen. Thawing can be at a range of temperatures, e.g., from about from about 0° C. to about 25° C., which is slow thawing; or from about 26° C. to 40° C., which is fast thawing. An example of rapid thawing is thawing the formulation in a 37° C. water bath. A protein in a formulation may be stable for at least one freeze-thaw cycle, at least five freeze-thaw cycles, or at least ten freeze-thaw cycles.

It may be desirable to determine an optimal regime for freeze-thawing a formulation to preserve stability, or it may be desirable to identify a formulation that provides the greatest stability for a protein that will be subjected to a particular freeze-thaw cycle. Accordingly, in some embodiments, this parameter is assessed. For example, a test formulation can be assayed for stability under a variety of freeze-thaw conditions such as rapid freezing, slow freezing, rapid thawing, slow thawing in various combinations to determine the procedure that produces the fewest degradation products (e.g., that has the greatest stability).

Polypeptides

Polypeptides used in the formulations described herein are generally isolated proteins. An "isolated" protein is substantially free of cellular material or other contaminating proteins from the cell or tissue source from which the protein is derived, or substantially free from chemical precursors or other chemicals when chemically synthesized. The language "substantially free" means a preparation of isolated protein having less than about 30%, 20%, 10% or 5% (by dry weight), of other proteins (also referred to herein as a "contaminating protein"), or of chemical precursors. When the isolated protein is recombinantly produced, it is also generally substantially free of culture medium, i.e., culture medium represents less than about 20%, less than about 10%, or less than about 5% of the volume of the protein preparation.

In some cases, combinations of proteins are used in a formulation. For example, two different antibodies that are to be prepared as a medicament can be stored together in the same formulation. An antibody can also be used with a formulation in combination with other types or proteins or peptides, including toxic peptides. Peptides or protein fragments can be used with the formulations, e.g., an antibody fragment such as a Fab fragment can be used.

In general, "protein" refers to a full-length protein or a fragment thereof. A protein can correspond to a naturally occurring protein or fragment thereof, or a genetically engineered protein originating from e.g., mutagenesis or recombinant techniques, or a fragment thereof. A protein can, in some cases include a non-proteinacious moiety such as a detectable molecule (e.g., a fluorescent molecule or a radioisotope), a toxin, a drug, or a small molecule. Proteins can contain, e.g., non-naturally occurring amino acids. The protein can be a hybrid protein. The protein can include more than one type of separate protein as in an antibody (e.g., containing both heavy and light chains) or a mature insulin protein. An example of a protein fragment that can be used includes a Fab fragment or an Fc fragment. In some cases, a peptide is used with a formulation, or, as described above, a combination of at least one protein and at least one peptide or protein fragment. Proteinaceous toxins can also be stored in formulations, e.g., alone, conjugated to another protein or peptide, or as a separate entity with another protein or peptide.

In general, the formulations provided herein are useful for any polypeptide (protein or peptide) as described herein for proteins.

A peptide is a compound having two or more covalently linked amino acids (e.g., 5, 10, 15, 20, 30, or 50 amino acids). In general, a protein is a polypeptide or multiple polypeptides (e.g., an antibody molecule containing heavy and light chains, or portions thereof) that are at least 50 amino acids in length.

The formulations can also be used to store polypeptides that are conjugated to a peptide or non-peptide moiety. Examples of such moieties include, without limitation, a fluorescent molecule (for example, fluorescein, rhodamine, green fluorescent protein (GFP), red fluorescent protein (RFP), Cy3, Cy3.5, Cy5, or Cy5.5), an elemental moiety (e.g., gold particles), a drug, or a toxin. Methods of conjugating such molecules to a polypeptide are known in the art. Examples of molecules include, without limitation, ricin (Mansfield et al., 1997, Blood 90:2020-2026; Ghetie et al., 1991, Cancer Res. 51:5876; Conry et al., 1995, J. Immunother. Emphas. Tumor Immunol. 18:231-241), *Pseudomonas* exotoxin A (PE) (Smith, 2001, Seattle Genetics Curr. Opin. Investig. Drugs 2(9):1314-1319; Mansfield et al., 1996, Bioconjug. Chem. 7:557), taxane (i.e., Paclitaxel) (Guillemard et al., 2001, Cancer Res. 61: 694-699), doxorubicin (Shouval et al., 1988, Proc. Nat. Acad. Sci. USA. 85:8276-8280; Takahashi et al., 1996, Anticancer Drugs 7(6):687-696; Shih et al., 1991, Cancer Res. 51(16):4192-4198; Shih et al., 1994, Cancer Immunol. Immunother. 38(2):92-98; Alexandru et al., 1999, Cancer Res. 59:115-121; Trail et al., 1993, Science 261:212-215), anthracenes (Dias et al., 2005, Bioconjugate Chem. 16:949-958), maytansinoid (Tassone et al., 2004, Cancer Res. 64:4629-4636; Tolcher et al., 2003, J. Clin. Oncol. 21(2):211-222), adriamycin (Hurwitz et al., 1983, Ann. N.Y. Acad. Sci. 417:125-36; Takahashi et al., 1988, Gan No Rinsho 34:847-50; Deguchi et al., 1987, J. Urol. 137(2):353-358), radioisotopes (Karube et al., 1996, Nuclear Med. Biol. 23:753-759; Mishra et al., 2004, J. Drug Target. 12(9-10):559-567; Lee et al., 2001, Cancer Res. 61:4474-4482), methotrexate (Ryser et al., 1988 J. Cell Physiol. 135(2):277-284; Mandel et al., 1991, J. Cell Physiol. 149(1):60-65),1,4,7,10-tetraazacyclododecane-N,N',N'',N'''-tetraacetic acid (DOTA), e.g., conjugated to another moiety such as 90-yttrium (Lu et al., 2005, J. Pharm. Sci. 94(4):788-797), streptavidin (Ngai et al., 1995, Nucl. Med. Biol. 22(1), 77-86), radioisotope conjugate products (e.g., listed in *Biopharmaceutical Products in the U.S. Market*, 4$^{th}$ *Edition*, Rader, ed., Biotechnology Information Institute, Rockville, Md., 2005), including technetium (Tc) 99m, yttrium, and In111 radioconjugates.

In general, the protein component of a formulation is a protein having a relatively high pI, for example, a pI of at least 6.0, 7.0, 8.0, or 8.5. The protein can have more than one peptide chain as in an antibody. When the protein component of a formulation is an antibody, the antibody can be polyclonal or monoclonal, or a fragment thereof (e.g., a Fab fragment). A protein can be present in a formulation at a concentration of from about 1 mg/ml to about 300 mg/ml, about 1 mg/ml to about 200 mg/ml, about 1 mg/ml to about 100 mg/ml, about 1 mg/ml to about 50 mg/ml, about 10 mg/ml to about 300 mg/ml, about 10 mg/ml to about 200 mg/ml, about 10 mg/ml to about 50 mg/ml, about 10 mg/ml to about 30 mg/ml, or about 20 mg/ml to about 50 mg/ml. Specific antibodies used in the formulations described herein are a humanized monoclonal anti-CD22 antibody, a monoclonal anti-Lewis Y antibody, and an anti-5T4 antibody.

An isolated protein used in a formulation is generally a protein that has potential as a therapeutic or potential to be part of a therapeutic. Such proteins are referred to herein as a therapeutic protein and include antibodies.

Examples of specific proteins that can be used as described herein include antibodies such as anti-CD-22 (see US20040082764A1 and US20040192900A1), anti-Lewis Y (WO 05/019271A1), and anti-5T4 (see U.S. Ser. No. 60/608494).

pH

Favorable pH conditions for a formulation are between about pH 4.0 to pH 8.0. In general, the pH is about 5.5-6.0. At a pH of about 5.5-6.0, a formulation containing a monoclonal antibody can be stored and retain stability for at least three months, e.g., six months, one year, or two years at 0° C. to about 8° C. (generally at about 1° C. to about 5° C.), and for long term storage (for at least three years, five years, seven years, or ten years) at, e.g., −80° C.

Identification of Favorable Formulations

In some methods described herein, a favorable formulation is identified for a specific protein of interest. In these methods, an isolated protein, e.g., a therapeutic protein such as an antibody, is identified that is to be stored in a formulation such as those described herein. The protein can be an antibody that is to be stored until it can be used for downstream processing such as to manufacture an antibody conjugated to a cytotoxin (e.g., calicheamicin) for use as a therapeutic. Other examples include storage of an antibody that is to be conjugated to a detectable label such as fluorescein, rhodamine, or conjugation to polyethylene glycol followed by lyophilization for longer storage of the antibody.

To identify a favorable formulation for storage of the isolated protein, the protein is generally suspended in a series of test solutions at a pH ranging from about 4.0-8.0 (e.g., pH 5.0-6.0) and salt concentrations ranging from about 0 mM-150 mM. These test solutions are stored at various temperatures for a specified period of time or for several different times (e.g., three days, two weeks, or four weeks). The samples are then evaluated for at least one parameter of stability such as high molecular weight species, low molecular weight species, a change in the percentage of acidic species, or a change in the amount of aggregates and high molecular weight species. Samples in which the protein component of the formulation is stable are then selected as favorable formulations for storage of the species. Additional evaluations can be carried out to evaluate other parameters of stability such as stability after freeze-thaw cycling or after agitation (shaking). The Examples provided supra provide additional guidance for methods of identifying a favorable formulation for storage of a specific isolated protein.

Methods of Storing a Protein

Methods of storing proteins or peptides (e.g., antibodies, antibody fragments, or proteins conjugated to a peptide or non-peptide moiety) are provided herein. The methods are particularly useful for storing a protein such as an antibody until it is needed for further manufacture, e.g., to manufacture a drug conjugated to a cytotoxin or to manufacture a detectably labeled reagent, or for storage of a protein that has been modified, for example, by conjugation to a peptide or non-peptide moiety.

Storage of a protein (e.g., antibody) as part of a claimed formulation provides increased flexibility for downstream processing compared to formulations that contain stabilizing agents and/or cryoprotectants.

A formulation can also be used to provide, e.g., stable monoclonal antibody drug substance, or drug substance intermediate formulation for further processing, such as for conjugation with potent anti-cancer agents, lyophilization, or liquid formulation for parental administration. In general, the method includes storage of a selected isolated protein as part of an aqueous solution that does not include a surfactant, does not include a cryopreservative, and has a relatively low buffer concentration (e.g., about 10 mM to about 20 mM). In general, the salt concentration of the formulation is relatively low, generally less than about 100 mM, e.g., about 0 mM to about 50 mM, about 1 mM to about 20 mM, about 1 mM to about 10 mM, or about 5 mM to about 10 mM.

In addition to the advantages described supra and those apparent from the claims, proteins stored as described herein have good reproducibility between samples (e.g., protein samples from a single preparation that are aliquoted and the aliquots stored using a formulation described herein). In addition, proteins stored as described herein are generally efficiently processed subsequent to storage, for example they are more efficiently conjugated than proteins stored with cryoprotectant and/or surfactant.

EXAMPLES

The invention is further illustrated by the following examples. The examples are provided for illustrative purposes only. They are not to be construed as limiting the scope or content of the invention in any way.

Example 1 pH

Anti-Lewis Y

To investigate the pH range in which an antibody is stable, samples of 1 mg/ml anti-Lewis Y were prepared in a pH range from 4 to 8, specifically at pH 4.0, 5.0, 5.5, 6.0, 6.5, 7.0, and 8.0. In this Example and those described below, samples were generally prepared in 5 ml Teflon® PFA vials (Cole-Parmer, Vernon Hills, Ill.), e.g., with a total sample volume of 2 ml. Protein concentrations were determined using UV absorbance at 280 nm measured with a Spectra Max® PLUS spectrophotometer (Molecular Devices Corp., Sunnyvale, Calif.) to assay samples in Costar® 96-well UV plates (Corning, Corning, N.Y.). Protein concentration was calculated using specific absorbance coefficient of 1.36 (mg/ml)$^{-1}$ cm$^{-1}$. The samples were prepared by dialysis into pH buffers containing 10 mM potassium phosphate buffer of the selected pH. Each sample also contained 75 mM NaCl. The prepared samples were sterile filtered and were placed in a −80° C. freezer, or in a stability chamber maintained at 5° C. or 40° C. After four weeks, the samples were assayed for the presence of high molecular weight species and low molecular weight species using SEC-HPLC (size exclusion chromatography-high performance liquid chromatography). SEC-HPLC analysis was performed using TosoHaas (Montgomeryville, Pa.) BIOSEP G3000SW$_{XL}$ as the separation column using methods known in the art.

Frozen samples were thawed in a water bath at 37° C. before analysis.

Figure 1B:
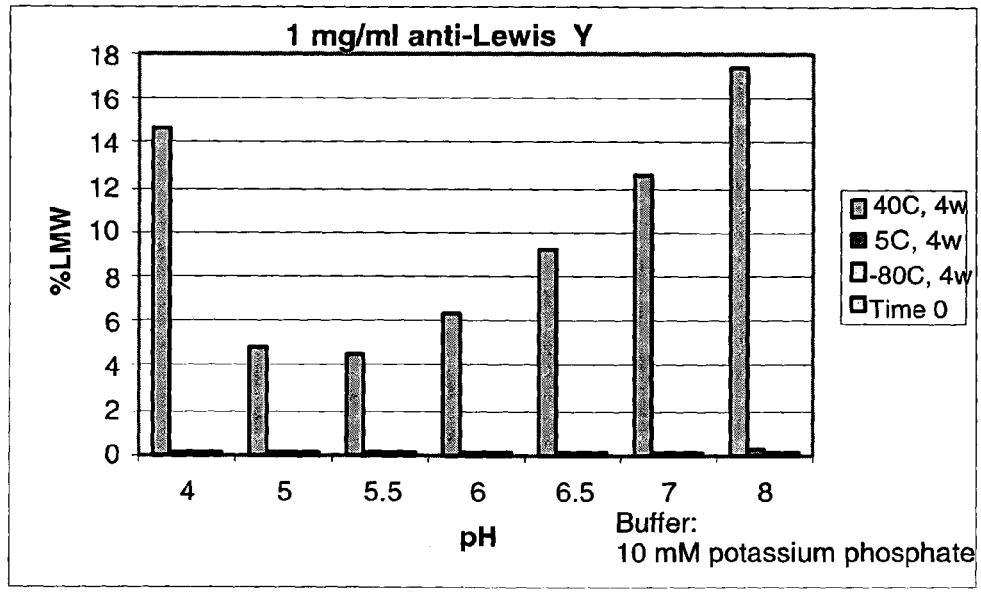
FIG. 1B is a bar graph depicting the results of SEC-HPLC analysis of 1 mg/ml anti-Lewis Y at various pHs and various temperatures. Results are expressed as percent low molecular weight (LMW) species.

The occurrence of high molecular weight species increased with pH, but high molecular weight species were not a major degradation product as a function of pH (FIG. 1A). The pH profile of low molecular weight species for the samples stored at 40° C. was V-shaped, with the minimum of low molecular weight species at pH 5.5 (FIG. 1B). Therefore, the anti-Lewis Y antibody was stable at a temperature range of −80° C. to 5° C. and over a pH range of from pH 4.0 to 8.0.

Figure 2:
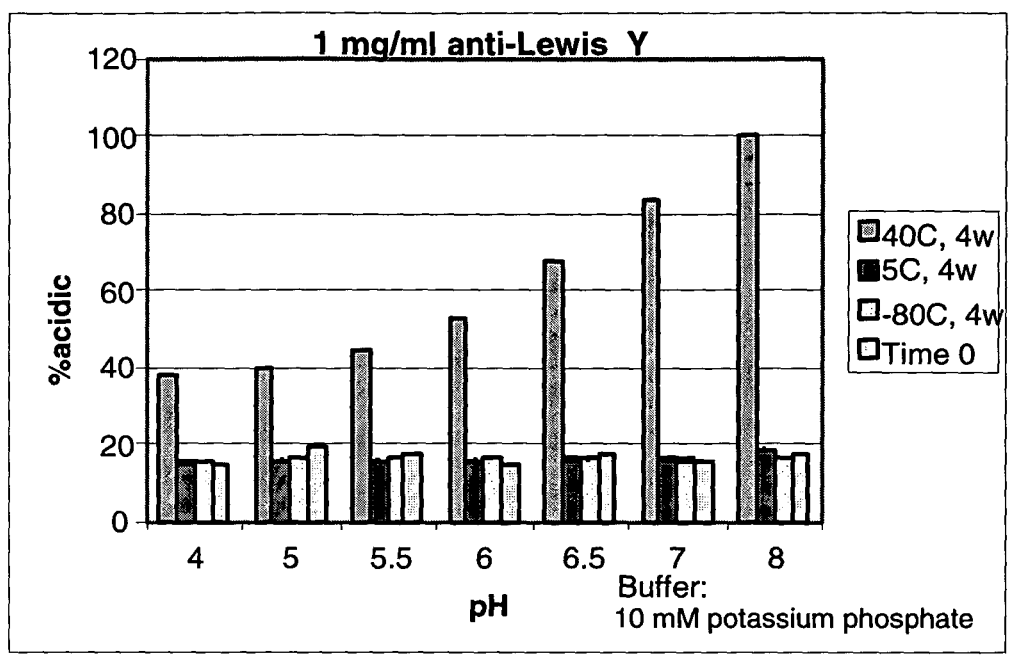
FIG. 2 is a bar graph depicting the results of CEX-HPLC analysis of 1 mg/ml anti-Lewis Y at various pHs and various temperatures. Results are expressed as percent acidic species.

CEX-HPLC (cation exchange chromatography-HPLC) was used to further assess the stability of the samples. These analyses were performed employing Dionex (Sunnyvale, Calif.) ProPac WCX-10 column. It was found that the concentration of acidic species increased at high pH in samples stored at 40° C. (FIG. 2). However, for samples stored at 5° C. and −80° C., the anti-Lewis Y was stable over the entire pH range, confirming the conclusions drawn from the SEC-HPLC data.

Figure 3:
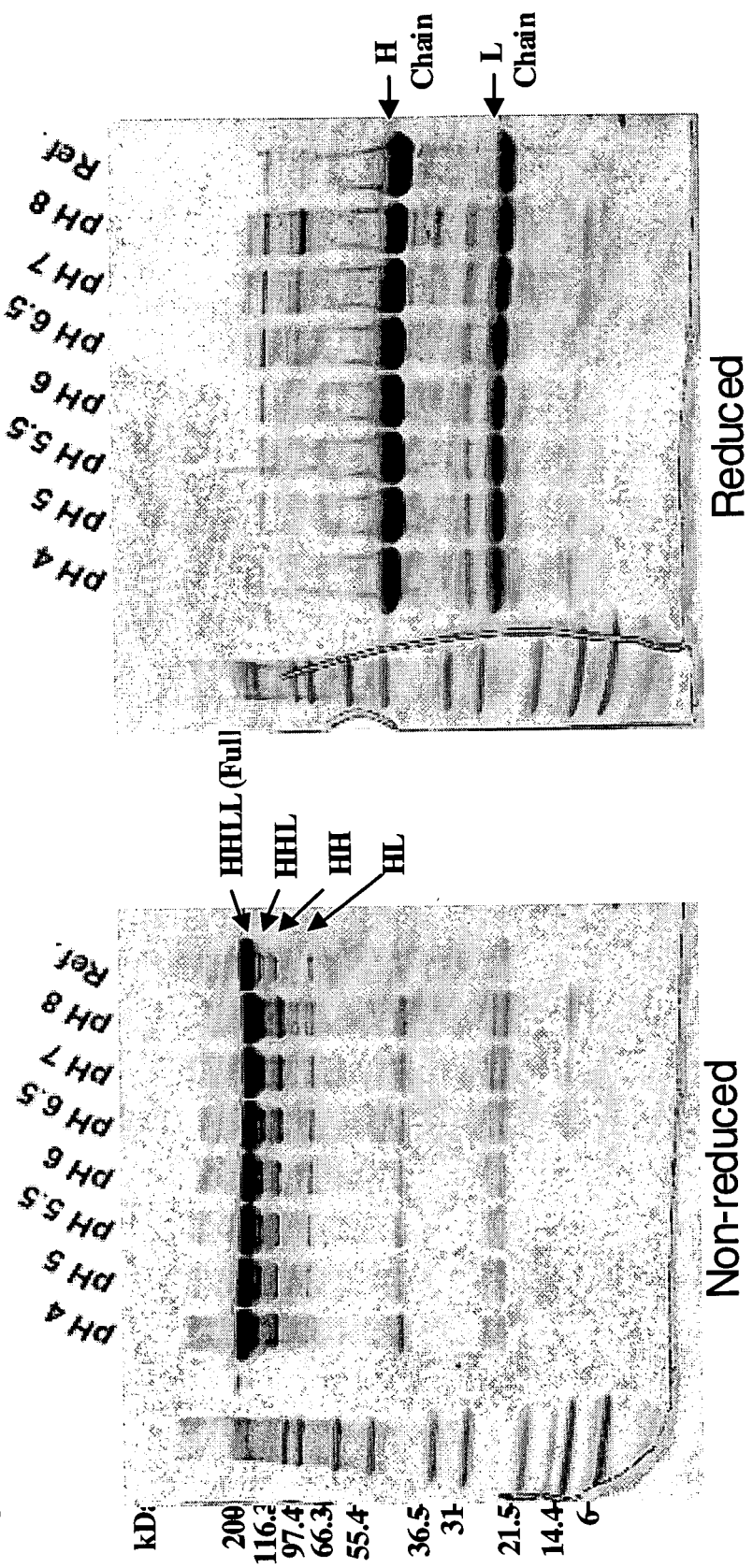
FIG. 3 is a depiction of an SDS-PAGE of anti-Lewis Y samples stored at 40° C. for four weeks at various pHs. The left image is of a gel run under non-reducing conditions and the right image is of a gel run under reducing conditions.

As yet another method of evaluating stability, SDS-PAGE was used to further analyze samples stored at 40° C. using 4-20% gels run under either reduced or non-reduced conditions. In these experiments, it was demonstrated that the least amount of change in molecular weight, and therefore the most stability, was of those samples in the pH range of 5.0-6.0 (FIG. 3). Therefore, samples (e.g., antibodies) that are to be stored at 40° C. are best maintained at a pH of between about 5.0 and 6.0.

Isoelectric focusing (IEF) electrophoresis was used to further evaluate the samples stored at 40° C. IEF electrophoresis was used to monitor the changes in pI of the antibody samples due to production of acidic species as a result of protein degradation.

Figure 4:
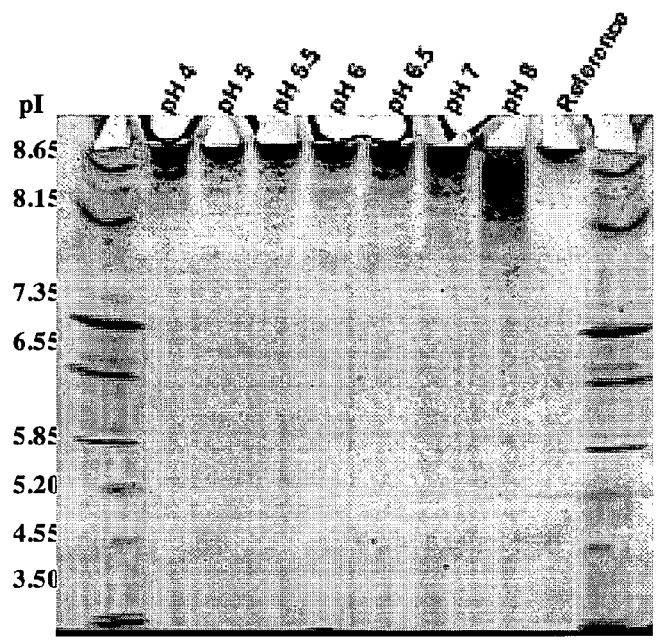
FIG. 4 is a depiction of an isoelectric focusing (IEF) gel of samples as described for FIG. 3.

Consistent with the results of SDS-PAGE analysis of the antibody samples, those samples in the pH range of 5.0-5.5 showed the least amount of change in overall protein charge (FIG. 4).

One important aspect of storage is the stability of the pH of a formulation over time. Therefore, the pH of the samples was assayed at the initiation of the experiment, after two weeks, and after four weeks of storage at all three temperatures. There was no significant deviation from the starting pH in any of the samples (Table 1).

TABLE 1 pH measurement of anti-Lewis Y pH screen stability samples

| | | Measured pH | | | | | |
|---|---|---|---|---|---|---|---|
| | | | 2 week | | | 4 week | |
| Target pH | Time 0 | −80° C. | 5° C. | 40° C. | −80° C. | 5° C. | 40° C. |
| 4.00 | 4.01 | 4.01 | 4.02 | 4.02 | 4.05 | 4.07 | 4.03 |
| 5.00 | 5.01 | 5.02 | 5.01 | 5.02 | 5.07 | 5.06 | 5.02 |
| 5.50 | 5.51 | 5.52 | 5.52 | 5.52 | 5.55 | 5.57 | 5.54 |
| 6.00 | 6.00 | 5.99 | 5.99 | 6.00 | 6.04 | 6.06 | 6.02 |
| 6.50 | 6.51 | 6.51 | 6.51 | 6.50 | 6.55 | 6.56 | 6.53 |
| 7.00 | 7.03 | 7.03 | 7.00 | 6.99 | 7.04 | 7.05 | 7.01 |
| 8.00 | 8.01 | 7.97 | 7.96 | 7.92 | 7.97 | 7.97 | 7.91 |

Together, the data presented supra demonstrate that the anti-Lewis Y is stable over a temperature range of −80° C. to 5° C. and over a pH range of 4-8. In general, a favorable pH for storage of this antibody is about 5.5. This also provides relatively favorable conditions for storage of the antibody at 40° C.

In general, a pH is selected for protein storage that results in stability over a range of two or more temperatures, for example, when the sample is stored below 0° C., when the sample is stored between about 0° C. and 15° C., and when the sample is stored between about 15° C. and 40° C. In another, non-limiting example, when the sample is stored at about −80° C., 5° C., and 40° C.

Anti-CD22

The effects of pH on storage of a second antibody (anti-CD22), a humanized IgG4 antibody that targets CD22, which is expressed on the surface of normal and malignant mature B-cells, were also tested. The theoretical pI of anti-CD22 is approximately 8.5. Whereas hydrolysis is likely to occur at pH 5.0 and below, deamidation is likely at pH greater than 7.5. Experiments were therefore designed to cover a pH range of 4 to 8 to test the effect of pH on the stability of the protein, to assess the stability-indicating capability of the analytical procedures, and to provide a rationale for the selection of the appropriate pH for a protein storage formulation.

Figure 5:
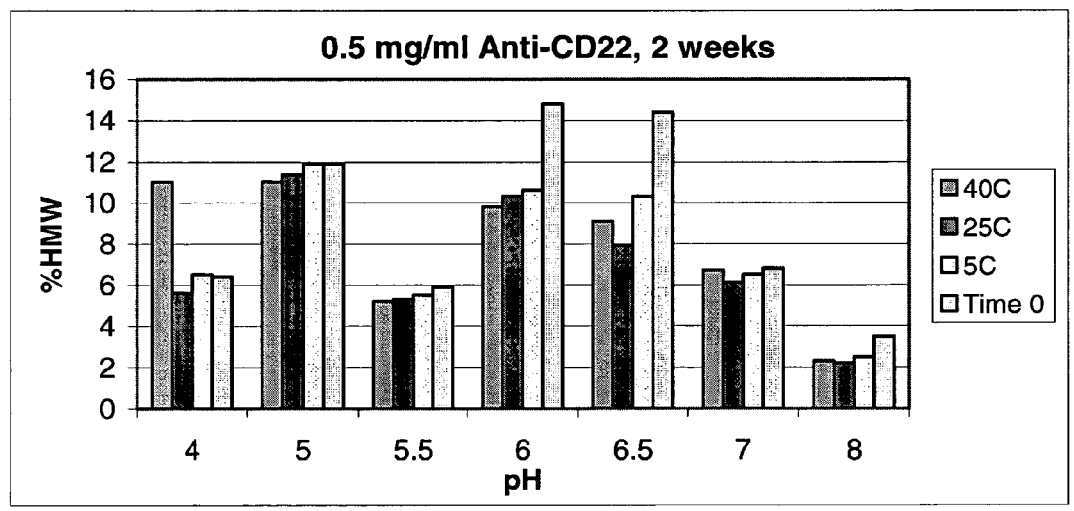
FIG. 5 is a bar graph depicting the results of SEC-HPLC analysis of 0.5 mg/ml anti-CD22 incubated for two weeks at various pHs and various temperatures. Results are expressed as percent HMW species.

Samples containing anti-CD22 were prepared containing 0.5 mg/ml anti-CD22 in various buffers at the pH values to be tested. Samples were stored for two weeks at 5° C., 25° C., or 40° C. at a pH of 4.0 (10 mM succinate), 5.0 (10 mM citrate), 5.5 (10 mM succinate), 6.0 (10 mM histidine), 6.5 (10 mM histidine), 7.0 (10 mM phosphate), or 8.0 (10 mM Tris). The samples were analyzed for the percentage of high molecular weight species present using SEC-HPLC. In these samples (each containing 0.5 mg/ml anti-CD22), there was no significant increase in the percent of high molecular weight species in those samples in the pH range of 5.0 to 8.0 compared to the amount present under initial conditions after two weeks (FIG. 5).

When an antibody such as an anti-CD22 is to be used for further (downstream) processing, consideration must be given to presentation of the intermediate substance in a buffer appropriate for the further processing. For example, conjugation of calicheamicin to an anti-CD22 can be performed in a buffer that contains no primary amine at pH 7 to 8.5. However, it may not be necessary for the intermediate substance to be provided in the conjugation buffer. In this example, the intermediate substance formulation will be constrained in that primary amines on buffer components would interfere with the conjugation procedure. To investigate storage of proteins in a solution that does not contain primary amines, experiments were conducted in which anti-CD22 was concentrated to 25 mg/ml and diafiltered or dialyzed into either 50 mM HEPES (pH 7.6), 50 mM succinate (pH 6.0), or 50 mM succinate+50 mM HEPES (pH 7.0). Each sample was tested for up to two weeks for stability. Samples were prepared with or without 75 mM NaCl and stored at −80° C., 4° C., or 40° C. Samples were analyzed at time =0, one week, and two weeks by $A_{280}/A_{320}$, SEC-HPLC, SDS-PAGE, and IEF (at two weeks).

Figure 6:
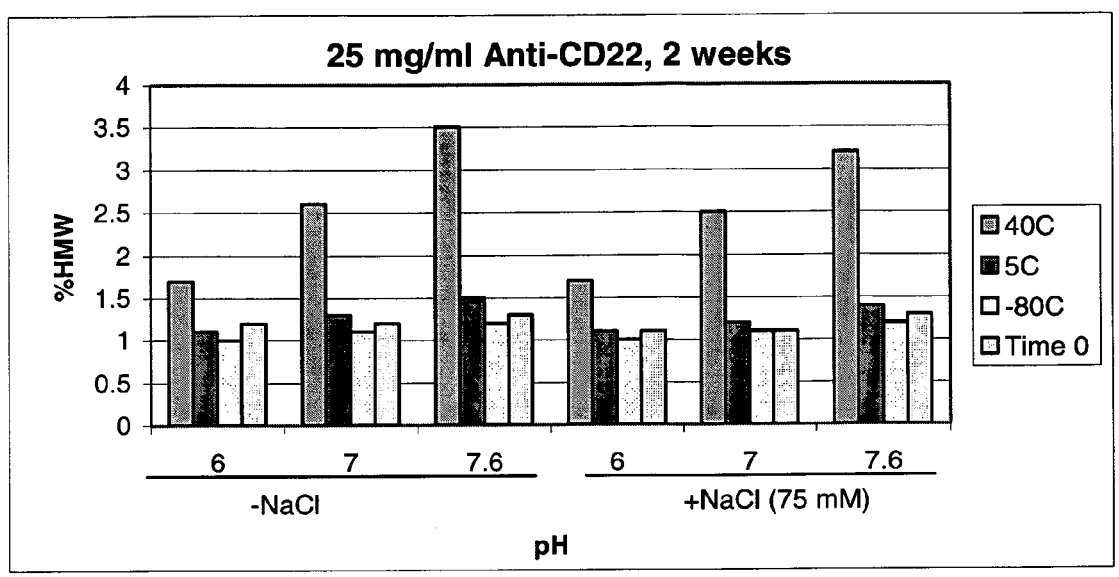
FIG. 6 is a bar graph depicting the results of SEC-HPLC analysis of 25 mg/ml anti-CD22 incubated for two weeks at various pHs, various temperatures, in the presence or absence of 75 mM NaCl. Results are expressed as percent HMW species.

The data from these experiments demonstrated that pH 6.0 (succinate buffer) provided greater stability than did pH 7.0 (HEPES) or a combination at pH 7.6 (HEPES and succinate) (FIG. 6).

SEC-HPLC was also used to evaluate the percentage of high molecular weight species in samples containing 25 mg/ml anti-CD22 at pH 6.0, 7.0, or 7.6 in succinate, HEPES, or a combination (as described supra) that were stored for two weeks at −80° C., 5° C., or 40° C., in the presence or absence of 75 mM NaCl. These data demonstrated that salt (NaCl) had no significant effect on the formation of high molecular weight species in these samples (FIG. 6). Therefore, the presence of salt is not a crucial condition for the storage of antibodies.

Example 2 pH/Buffers

Figure 7A:
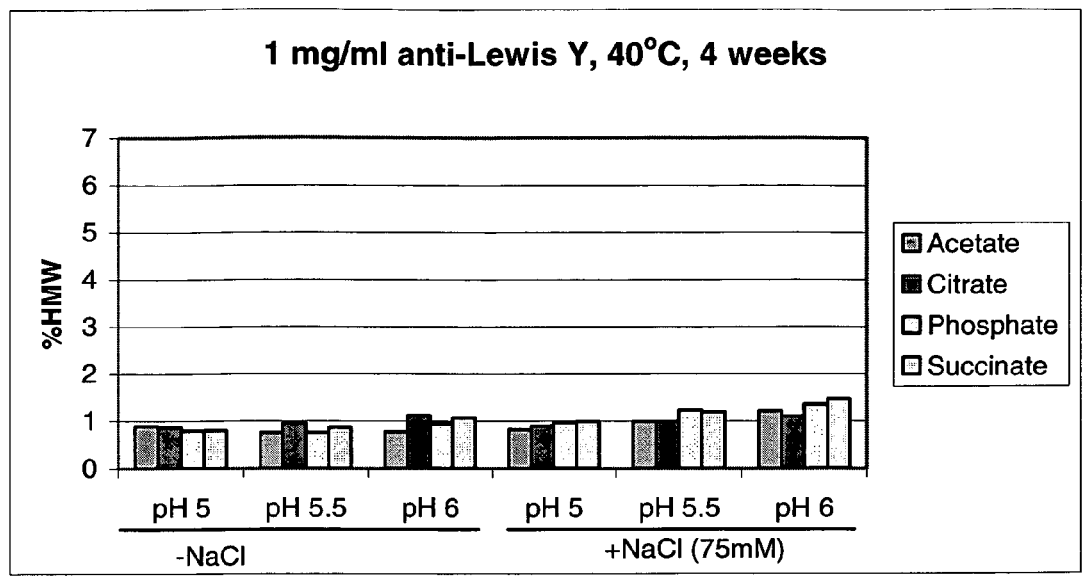
FIG. 7A is a bar graph depicting the results of SEC-HPLC analysis of 1 mg/ml anti-Lewis Y, incubated for four weeks at various pHs at 40° C., in various buffers, and in the presence or absence of 75 mM NaCl. Results are expressed as percent HMW species.
Figure 7B:
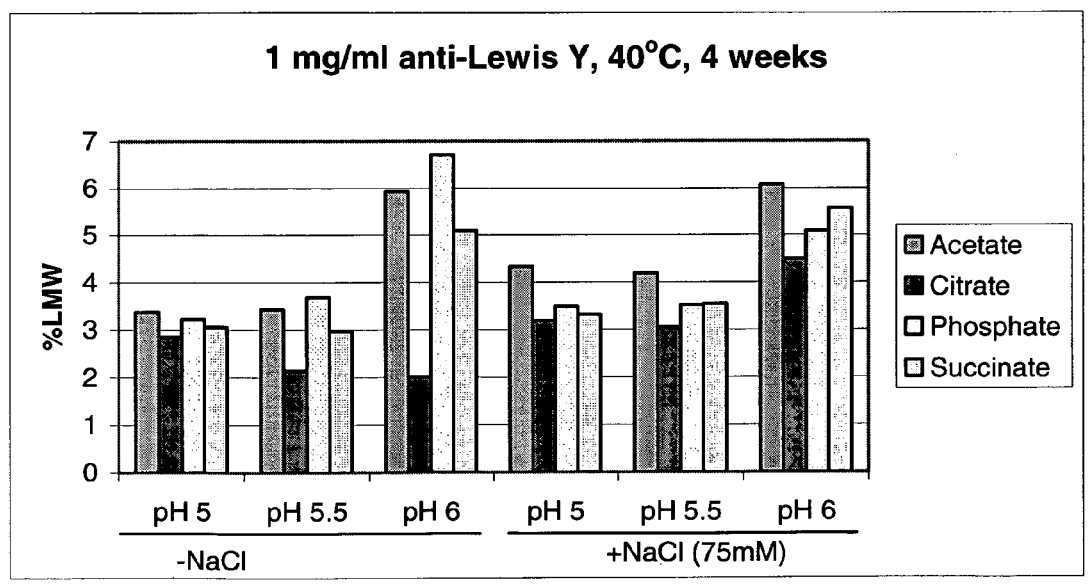
FIG. 7B is a bar graph depicting the results of SEC-HPLC analysis of 1 mg/ml anti-Lewis Y, incubated for four weeks at various pHs at 40° C., in various buffers, and in the presence or absence of 75 mM NaCl. Results are expressed as percent LMW species.

To determine whether different buffers provide favorable storage conditions at different pHs, buffers were tested at a pH 0.5 units above and below the tentative "optimal" pH using the anti-Lewis Y antibody as the stored sample. In these experiments, four different buffer systems were tested in the pH range from 5.0 to 6.0. The effect of various ionic strengths on stability was also evaluated. The buffers used in these experiments were 10 mM sodium acetate, pH 5.0, 5.5, and 6.0; 10 mM sodium acetate, 75 mM NaCl, pH 5.0, 5.5 and 6.0;

10 mM sodium citrate, pH 5.0, 5.5, and 6.0; 10 mM sodium citrate, 75 mM NaCl, pH 5.0, 5.5 and 6.0; 10 mM sodium phosphate, pH 5.0, 5.5, and 6.0; 10 mM sodium phosphate, 75 mM NaCl, pH 5.0, 5.5, and 6.0; 10 mM sodium succinate, pH 5.0, 5.5, and 6.0; and 10 mM sodium succinate, 75 mM NaCl, pH 5.0, 5.5, and 6.0. In these experiments, anti-Lewis Y was dialyzed into the above buffers and diluted to a final concentration of 1 mg/ml. The samples were then stored at −80° C. or 40° C. for up to 4 weeks, then analyzed for the percentage of high molecular weight species and the percentage of low molecular weight species using SEC-HPLC. In these experiments, it was found that high molecular weight species were not the major degradant, and the difference in the level of high molecular weight species between the different formulations was negligible (FIG. 7A). At pH 5.5, the sodium citrate sample demonstrated the lowest level of low molecular weight species among all of the buffers (with or without addition of NaCl) (FIG. 7B).

The samples were further analyzed using CEX-HPLC. These data confirmed the overall observations from the SEC-HPLC data in that there was an increased percentage of acidic species present in the of higher pH samples in all four buffers tested (FIG. 8), i.e., there is an upward trend of acidic species for all buffers in the pH range of 5.0 to 6.0.

These data demonstrate that overall, the stability of anti-Lewis Y was similar in all four tested buffers (Na acetate, citrate, phosphate, and succinate) in a pH range of 5.0 to 6.0. Furthermore, in the accelerated stability study (examining stability at 40° C.; FIG. 7B), the lowest amount of low molecular weight species formation was in the sample containing Na citrate buffer. Therefore, a favorable buffer for the anti-Lewis Y is 10 mM Na citrate, pH 5.5. These data also demonstrate a method of identifying a favorable formulation for storage of a protein such as an antibody.

Example 3

Salt Concentration and Protein Concentration

Salt concentration was examined as a parameter that may have an effect on stability of a protein in a storage formulation. Storage stability at low protein concentration was also evaluated in the accelerated degradation protocol described in Example 2. In these experiments, it was found that at a protein concentration of 1 mg/ml, the addition of NaCl slightly promoted low molecular weight species formation (FIG. 7B) while it suppressed acidic species formation (FIG. 8) in all buffers tested.

Figure 8:
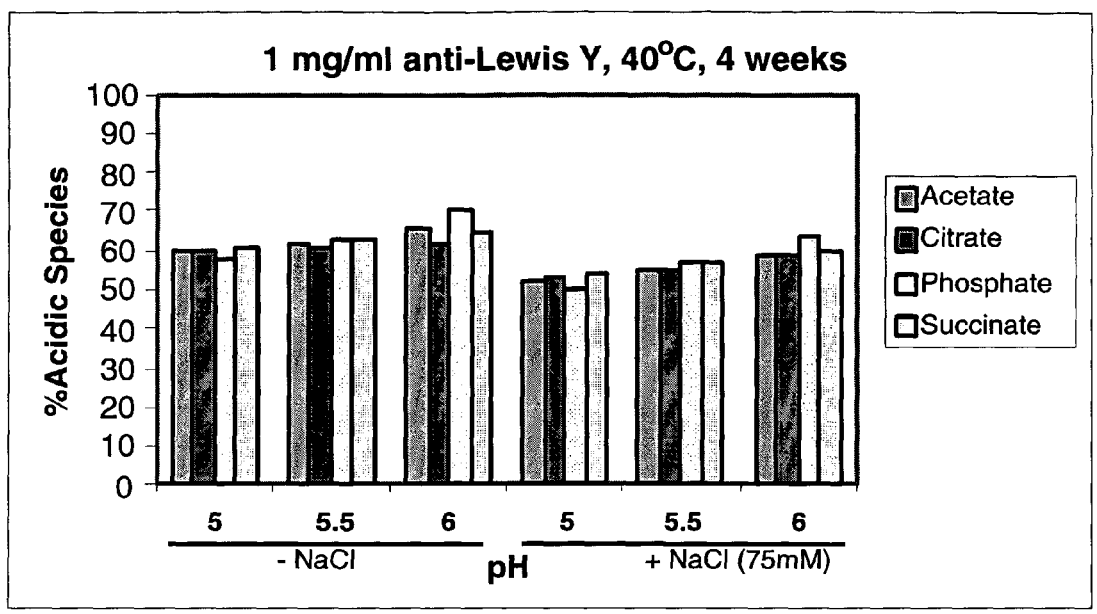
FIG. 8 is a bar graph depicting the results of CEX-HPLC analysis of 1 mg/ml anti-Lewis Y incubated for four weeks at various pHs at 40° C. in various buffers, and in the presence or absence of 75 mM NaCl. Results are expressed as percent acidic species.
Figure 9A:
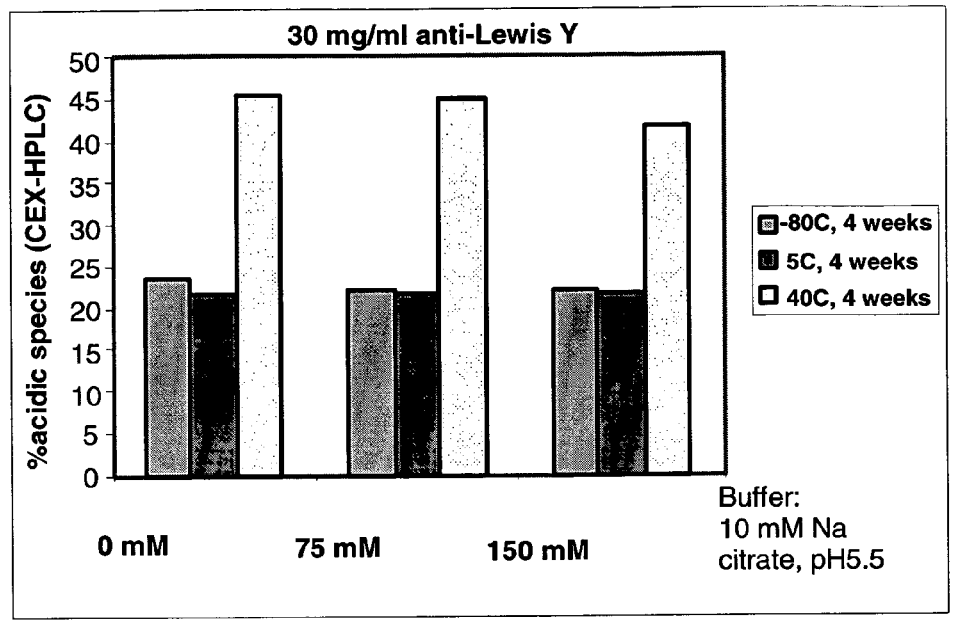
FIG. 9A is a bar graph depicting the results of CEX-HPLC analysis of 30 mg/ml anti-Lewis Y incubated for four weeks in 10 mM Na citrate, pH 5.5 at various temperatures and various NaCl concentrations. Results are expressed as percent acidic species.
Figure 9B:
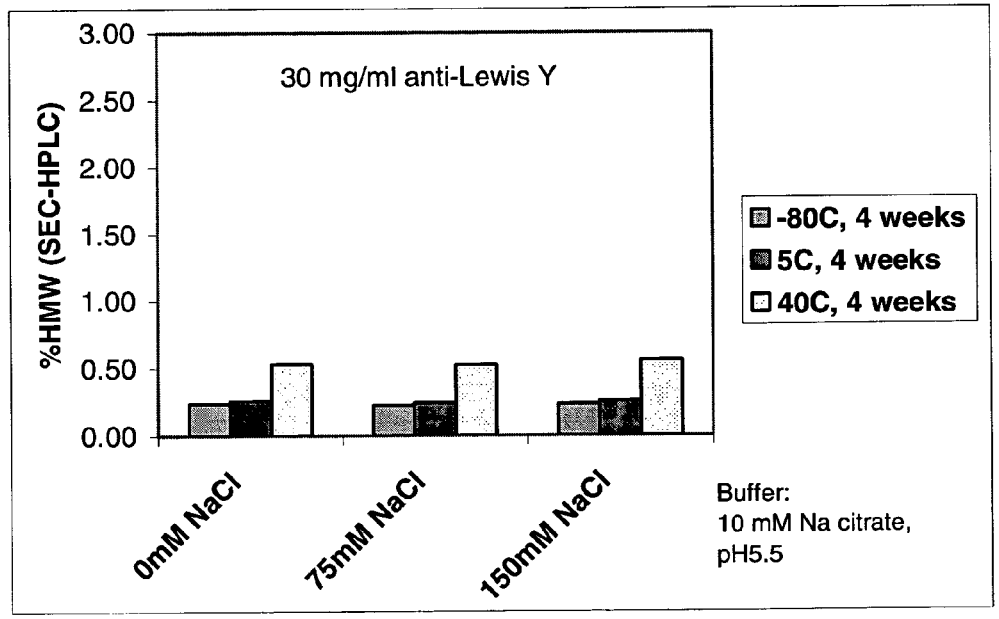
FIG. 9B is a bar graph depicting the results of SEC-HPLC analysis of the samples described for 9A. Results are expressed as percent HMW species.
Figure 9C:
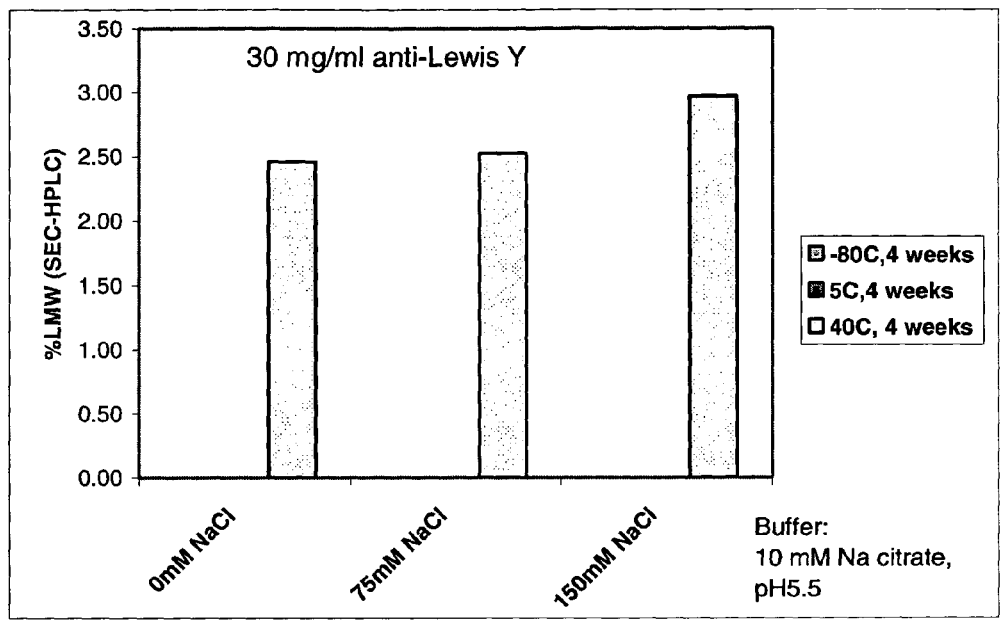
FIG. 9C is a bar graph depicting the results of SEC-HPLC analysis of the samples described for 9A. Results are expressed as percent LMW species.

CEX-HPLC and SEC-HPLC were used to evaluate the stability of anti-Lewis Y in 10 mM Na citrate pH 5.5 containing different molarities of NaCl. These data demonstrated that the anti-Lewis Y was stable at 5° C. and −80° C. in 10 mM Na citrate, pH 5.5 containing 0-150 mM NaCl (FIG. 9A). Accelerated degradation shows, at 30 mg/ml protein concentration, NaCl suppresses appearance of acidic species (FIG. 9A) but elevated low molecular weight species formation (FIG. 9C) and high molecular weight species formation was relatively stable under the different conditions (FIG. 9B), which confirms the observation from samples containing 1 mg/ml protein (FIGS. 7 and 8). Thus, a salt concentration of 75 mM NaCl was found to be the most favorable for minimizing overall degradation.

Stability with Shaking

Another condition that can affect stability of a protein is the amount of agitation undergone by the sample. Therefore, it is desirable that a storage formulation preserves a certain amount of stability when the sample is agitated. Experiments were performed to test the stability of anti-Lewis Y in a formulation under various conditions and incubated with agitation. In these experiments, formulations containing either 1 mg/ml or 30 mg/ml anti-Lewis Y in 10 mM Na citrate, pH 5.5 in the presence or absence of 150 mM NaCl was tested by shaking at 360 rpm for 24 hours at room temperature and the percent monomer recovery assayed using SEC-HPLC.

Figure 10:
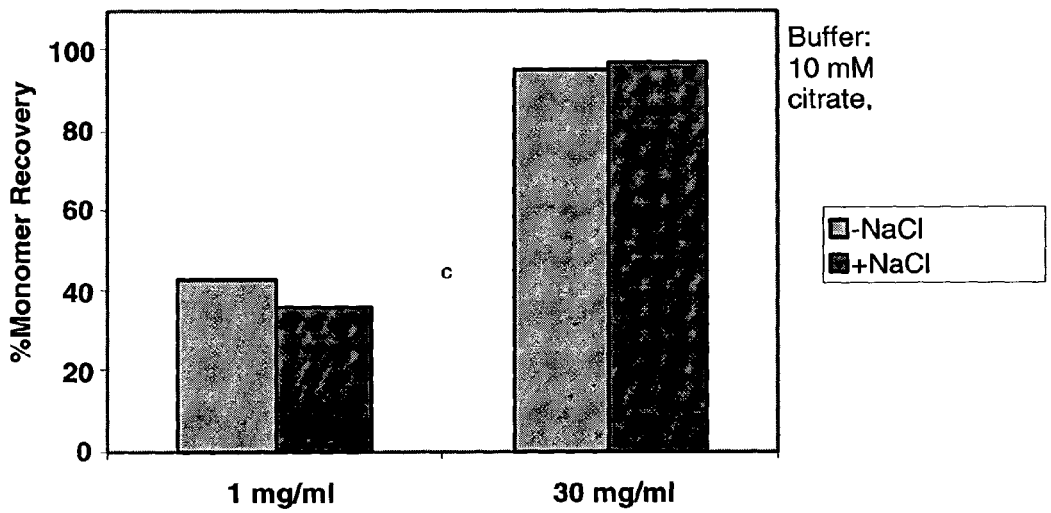
FIG. 10 is a bar graph depicting the results of SEC-HPLC of anti-Lewis Y at 1 mg/ml or 30 mg/ml in various salt concentrations and subjected to shaking. Results are expressed as percent monomer recovery.

These experiments demonstrated that the antibody was stable when present at a concentration of 30 mg/ml when subjected to shaking (FIG. 10). It was also found that at 1 mg/ml, NaCl slightly reduced recovery of monomer.

Accordingly, the simple storage formulation can provide sufficient protection from stress to the sample induced by shaking.

Stability Under Freeze/Thaw

Proteins to be used for various manufacturing methods may necessarily be subjected to freeze-thaw cycles, indeed, sometimes to multiple freeze-thaw cycles. It is, therefore, advantageous for a storage formulation to provide conditions under which there is minimal degradation caused by freeze-thaw cycles. In addition, it is useful to determine what conditions for freezing and thawing provide optimal preservation of the protein. To test these parameters, samples were prepared containing anti-Lewis Y at either 1 mg/ml or 30 mg/ml in 10 mM Na citrate, pH 5.5, in the presence of absence of 150 mM NaCl. These samples were then subjected to ten freeze-thaw cycles with fast freeze/fast thaw, fast freeze/slow thaw, slow freeze/fast thaw, or slow freeze/slow thaw conditions. Fast freeze was performed by freezing the sample in liquid nitrogen and slow freeze was performed by placing the sample at −80° C. Fast thaw was performed by thawing the sample in a 37° C. water bath and slow thaw was performed by placing the sample at room temperature. The amount of monomer was then evaluated in each sample using SEC-HPLC.

Figure 11A:
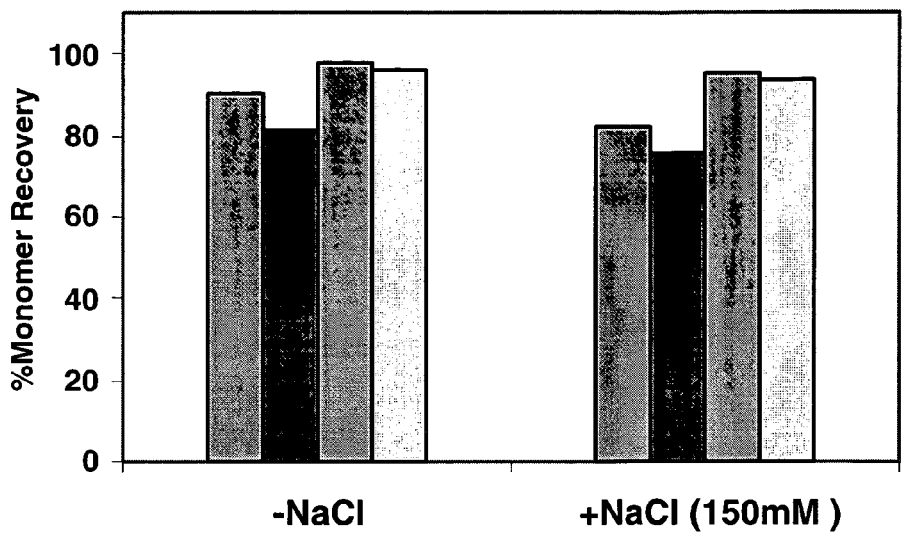
FIG. 11A is a bar graph depicting the results of SEC-HPLC of anti-Lewis Y at 1 mg/ml in 10 mM Na citrate, pH 5.5 in the presence or absence of 150 mM NaCl following ten freeze-thaw cycles as indicated in FIG. 11B. Results are expressed as percent monomer recovery.
Figure 11B:
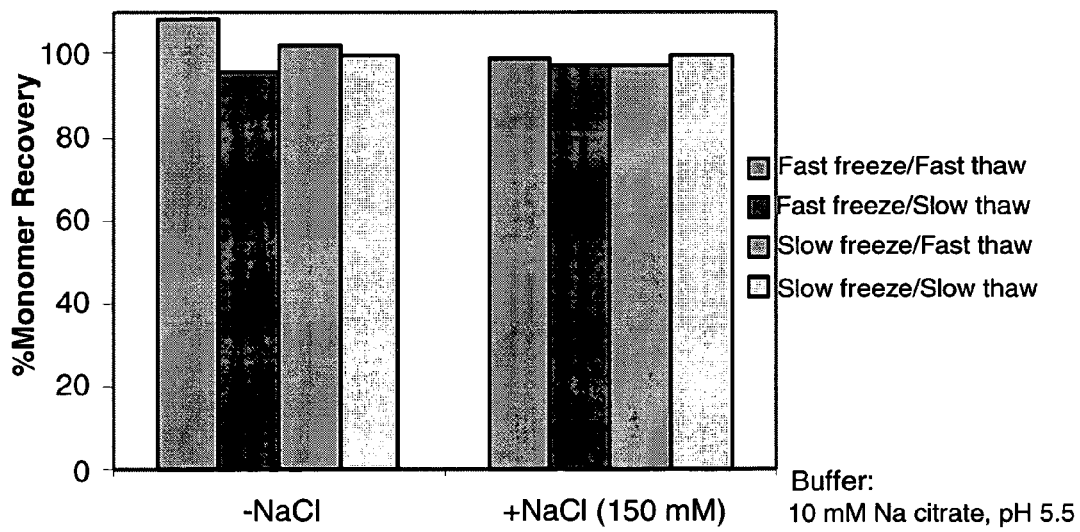
FIG. 11B is a bar graph depicting the results of SEC-HPLC analysis of anti-Lewis Y at 30 mg/ml in 10 mM Na citrate, pH 5.5 in the presence or absence of 150 mM NaCl following ten freeze thaw cycles as indicated. Results are expressed as percent monomer recovery.

The results of these experiments showed that the anti-Lewis Y was stable at high protein concentration (30 mg/ml) regardless of the freeze/thaw conditions or NaCl concentration (FIG. 11A and FIG. 11B). The anti-Lewis Y was stable under slow freezing conditions regardless of protein concentration, thaw conditions, or NaCl concentration. However, at 1 mg/ml, NaCl in the formulation slightly reduced recovery under fast freezing conditions.

In view of the above, it can be concluded that the anti-Lewis Y is stable at −80° C. and 5° C. in a NaCl concentration ranging from 0 mM-150 mM. In addition, an accelerated stability study (a study of formulations at 40° C.) showed that NaCl slightly decreased acidic species formation while promoting an appearance of low molecular weight species. In view of these results, 75 mM NaCl was found to be optimal for minimizing overall degradation of the anti-Lewis Y.

These experiments also demonstrate methods for identifying favorable conditions for a specific protein to be stored in a formulation described herein.

Anti-CD22

To examine the variability of storage conditions between different proteins and further validate the methods of identifying storage formulations for a specific protein, the storage stability of an anti-CD22 was investigated. In these experiments, formulations containing 25 mg/ml (FIG. 6) anti-CD22 were prepared in various buffers to achieve the desired pH; pH 6.0 (50 mM succinate); pH 7.0 (50 mM succinate and 50 mM HEPES); pH 7.6 (50 mM HEPES), and stored for one month at −80° C., 5° C., 25° C., or 40° C., then evaluated for the percentage of high molecular weight species.

Figure 12:
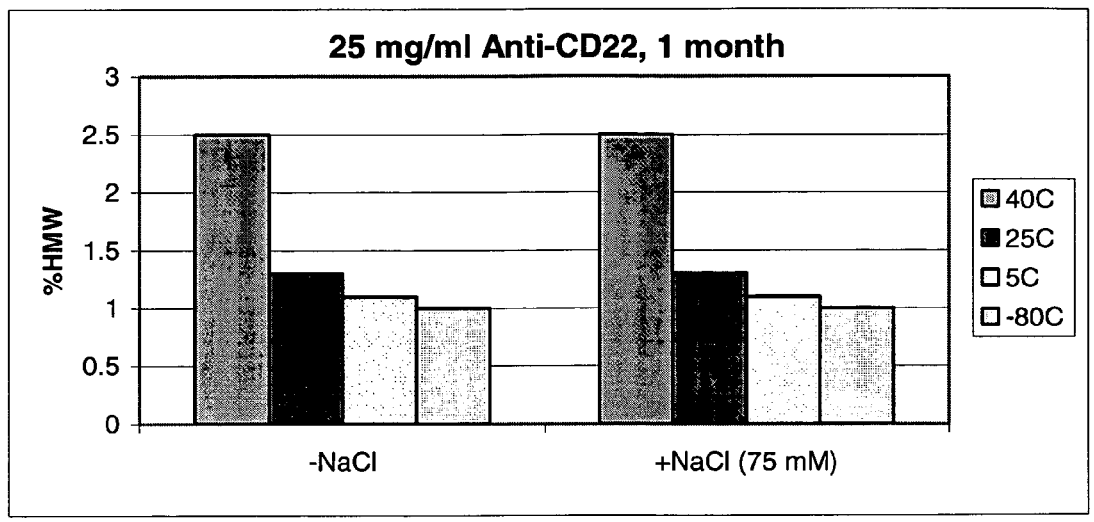
FIG. 12 is a bar graph depicting the results of SEC-HPLC analysis of 25 mg/ml anti-CD22 in 50 mM succinate, pH 6.0, incubated for one month at various temperatures in the presence or absence of 75 mM NaCl.

It was found that NaCl had no effect on anti-CD22 storage stability at high protein concentrations (FIG. 6 and FIG. 12) at any of the tested temperatures.

Stability Under Shaking Stress

Figure 13:
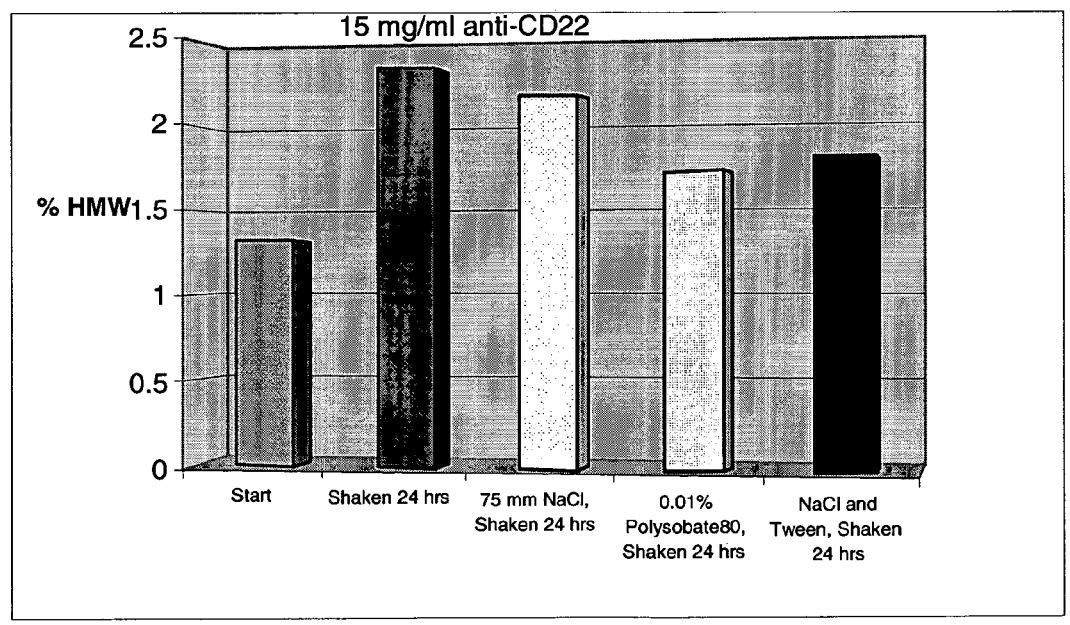
FIG. 13 is a bar graph depicting the results of SEC-HPLC analysis of 15 mg/ml anti-CD22 in 20 mM succinate, pH 6.0, succinate plus 75 mM NaCl, succinate plus 0.01% polysorbate 80, or succinate plus 75 mM NaCl and polysorbate 80 (Tween). Samples were shaken for 24 hours before analysis. A non-shaken control of protein in succinate buffer is included. Results are expressed as percent HMW species.

A shaking study was performed to determine surface/air interaction effects on anti-CD22 in the presence of NaCl and polysorbate 80. This study was also performed to assess the stability of anti-CD22 as a liquid during shipment and manufacturing. In these experiments, samples were prepared containing 15 mg/ml anti-CD22 in 20 mM succinate buffer, pH 6.0, an addition of 75 mM NaCl, 0.1% polysorbate 80, or 75 mM NaCl plus 0.1% polysorbate 80 (Tween). Samples were shaken at 300 rpm for 24 hours. A control was also prepared that contained only the anti-CD22 in succinate buffer. The percentage of high molecular weight species was then assayed. These data demonstrate that neither NaCl nor polysorbate 80 are beneficial to the stability of anti-CD22 during shaking (FIG. 13).

Overall, the data presented above for anti-CD22 in a storage formulation demonstrate that NaCl has no substantial effect on anti-CD22 overall stability. Therefore, NaCl is not necessary in anti-CD22 formulation.

Example 4

Antibody Concentration

The effects of protein concentration on storage stability in a formulation were examined. Determination of a favorable protein concentration is desirable when identifying a storage formulation for a specific protein, as well as discovering general principles related to the importance of this parameter in a formulation.

Figure 14A:
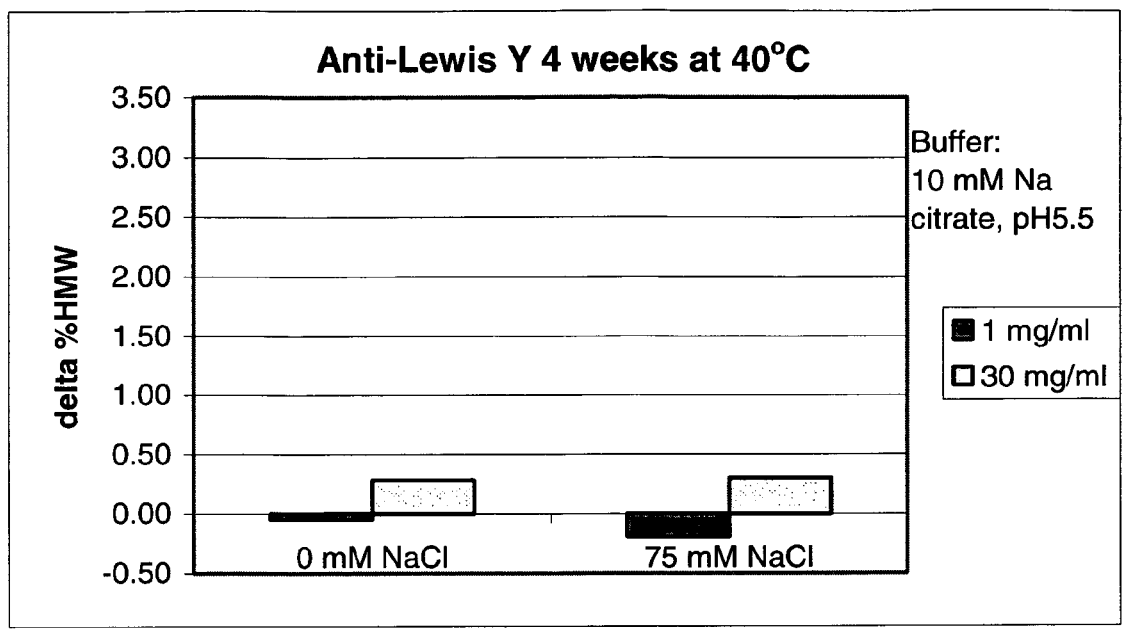
FIG. 14A is a bar graph depicting the results of SEC-HPLC analysis of anti-Lewis Y at 1 mg/ml or 30 mg/ml in 10 mM Na citrate, pH 5.5 incubated in the presence or absence of 75 mM NaCl for four weeks at 40° C. Results are expressed as a change in the percent HMW species.
Figure 14B:
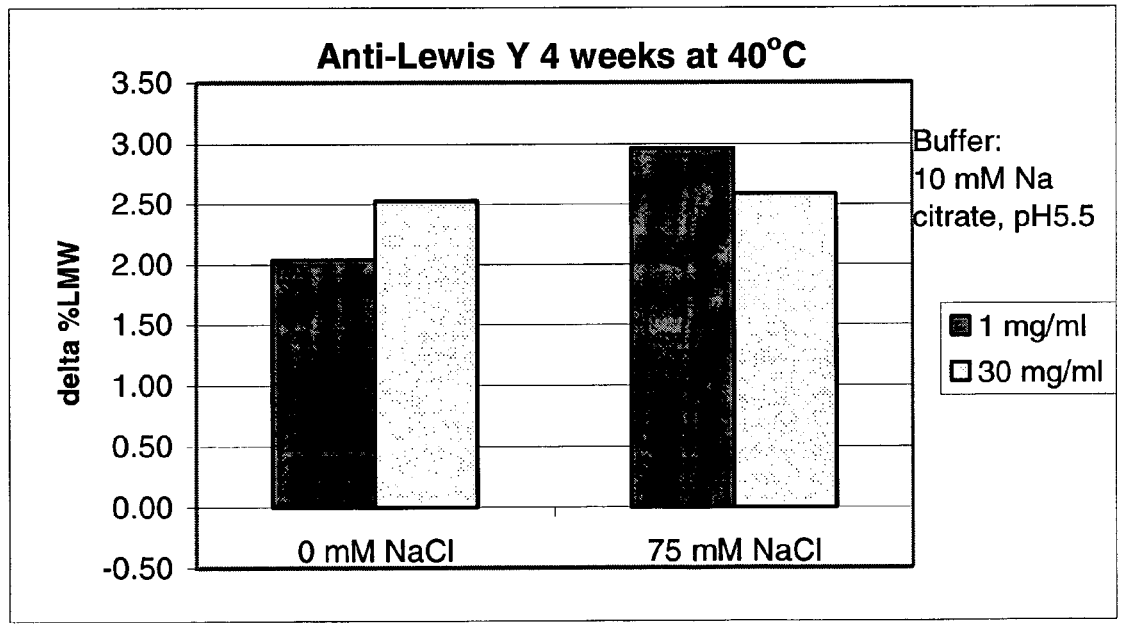
FIG. 14B is a bar graph depicting the results of SEC-HPLC analysis of anti-Lewis Y at 1 mg/ml or 30 mg/ml in 10 mM Na citrate, pH 5.5 incubated in the presence or absence of 75 mM NaCl for four weeks at 40° C. Results are expressed as a change in the percent LMW species.
Figure 14C:
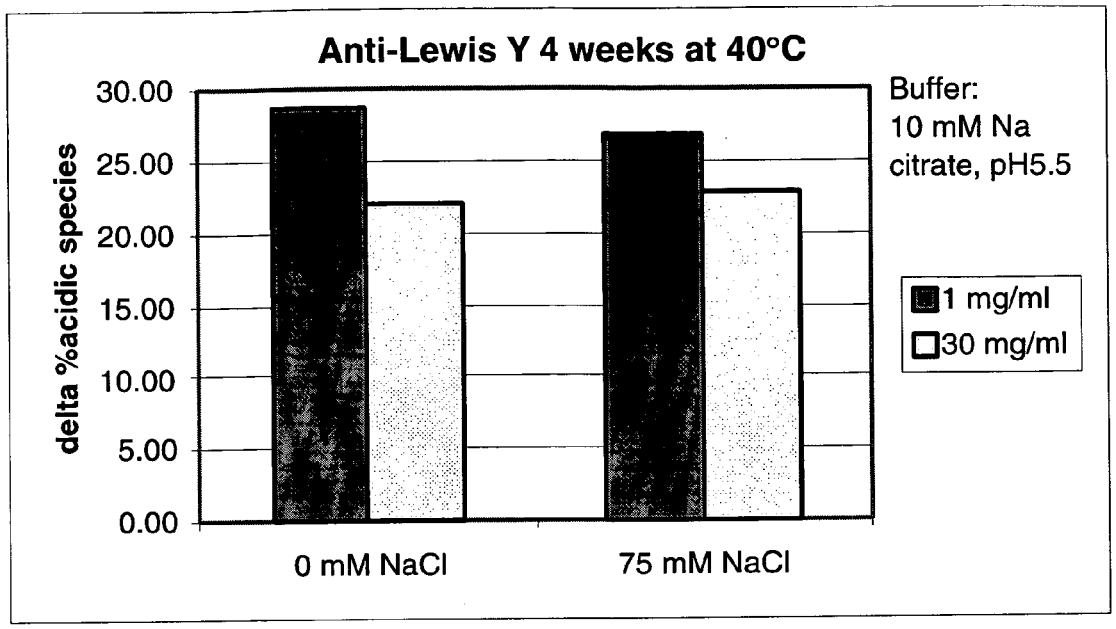
FIG. 14C is a bar graph depicting the results of CEX-HPLC analysis of anti-Lewis Y at 1 mg/ml or 30 mg/ml in 10 mM Na citrate, pH 5.5 incubated in the presence or absence of 75 mM NaCl for four weeks at 40° C. Results are expressed as a change in the percent acidic species.

In these experiments, samples were prepared containing anti-Lewis Y in 10 mM citrate, pH 5.5 at a concentration of 1 mg/ml or 30 mg/ml and containing either no NaCl or 75 mM NaCl. Samples were stored for four weeks at 40° C., then assayed for change in the percentage of high molecular weight species (FIG. 14A), change in the percentage of low molecular weight species (FIG. 14B), and change in the percentage of acidic species (FIG. 14C).

The results of these experiments revealed comparable stability for formulations containing 1 mg/ml and 30 mg/ml, with the lower concentration (1 mg/ml) only slightly more sensitive to the presence of NaCl.

Figure 15A:
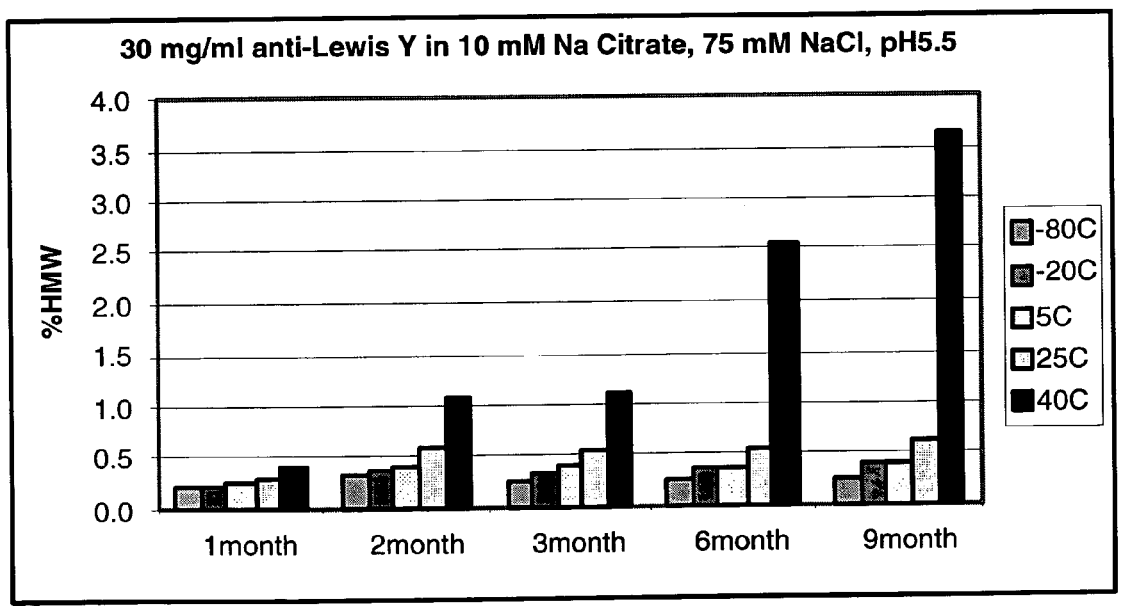
FIG. 15A is a bar graph depicting the results of SEC-HPLC analysis of anti-Lewis Y at 30 mg/ml in 10 mM Na citrate, pH 5.5 and 75 mM NaCl incubated at various temperatures for various times. Results are expressed as percent HMW species.
Figure 15B:
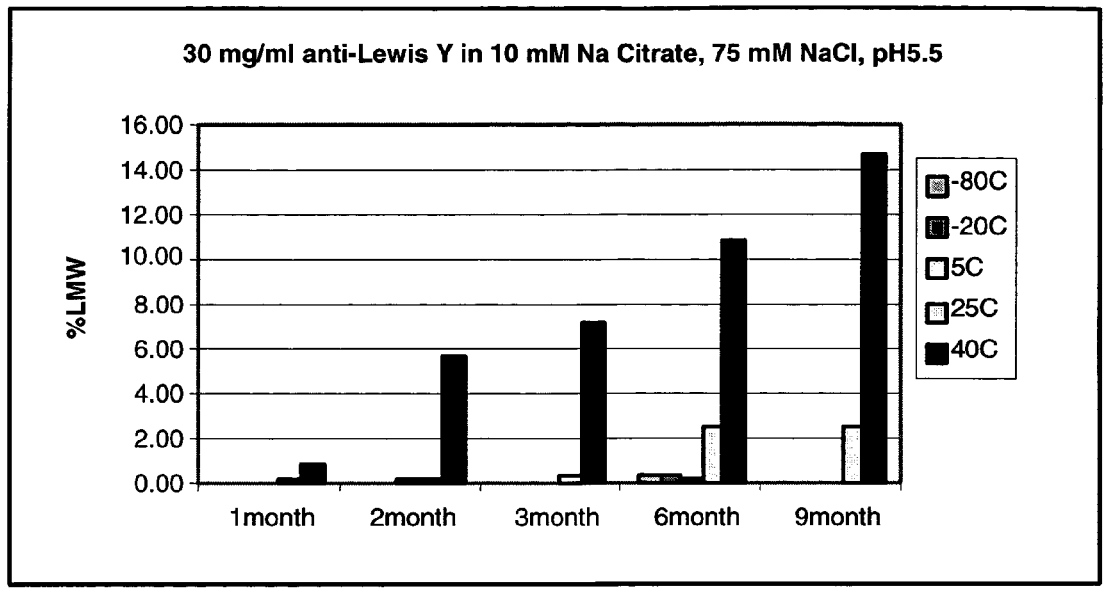
FIG. 15B is a bar graph depicting the results of SEC-HPLC analysis of anti-Lewis Y at 30 mg/ml in 10 mM Na citrate, pH 5.5 and 75 mM NaCl incubated at various temperatures for various times. Results are expressed as percent LMW species.
Figure 15C:
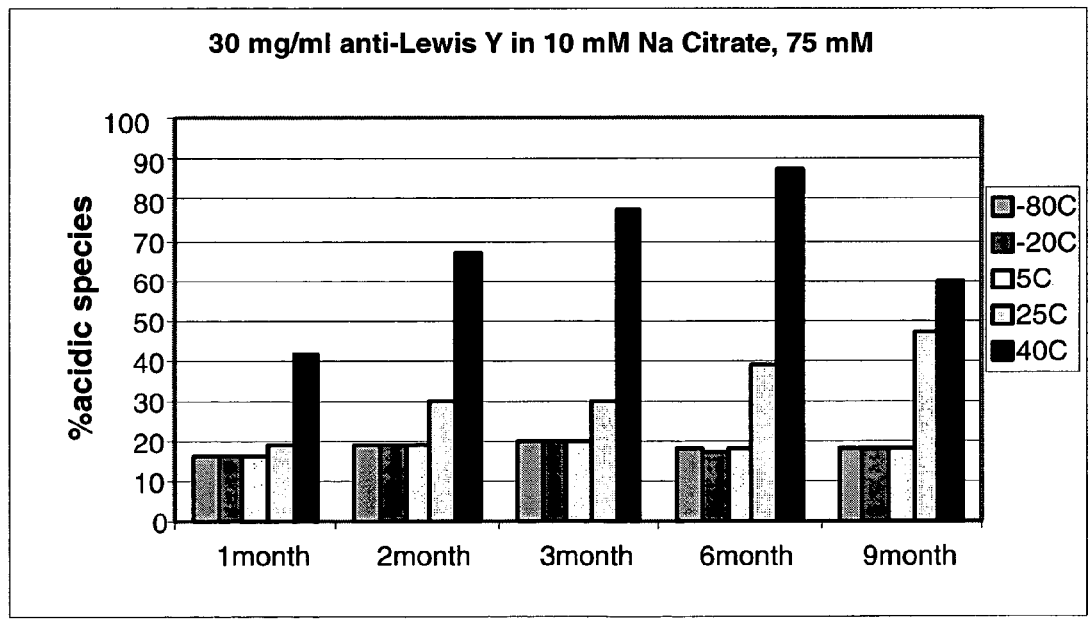
FIG. 15C is a bar graph depicting the results of CEX-HPLC analysis of anti-Lewis Y at 30 mg/ml in 10 mM Na citrate, pH 5.5 and 75 mM NaCl incubated at various temperatures for various times. Results are expressed as percent acidic species.

Sustained stability is particularly desirable in a storage formulation. Accordingly, a study was carried out to determine the stability of 30 mg/ml anti-Lewis Y formulations containing 30 mg/ml anti-Lewis Y in 10 mM Na citrate, pH 5.5 and 75 mM NaCl at various temperatures: –80° C., –20° C., 5° C., 25° C., and 40° C. Samples were tested at one month, two months, three months, six months, and nine months for the percentage of high molecular weight species (FIG. 15A), the percentage of low molecular weight species (FIG. 15B), and the percentage of acidic species (FIG. 15C). Analysis of these data demonstrated that there was good protein stability of anti-Lewis Y after 9 months of storage at a temperature range from –80° C. to 5° C. in the formulation 10 mM Na citrate, 75 mM NaCl, pH5.5.

Freeze/Thaw and Shaking Stability

As shown above, (FIG. 10 and FIG. 11), it appeared that anti-Lewis Y is not sensitive to shaking and freeze/thaw stress at a concentration of 30 mg/ml. In addition, the anti-Lewis Y was not sensitive to slow freezing at a concentration of 1 mg/ml regardless of thawing rate, but loss of protein was found at a concentration of 1 mg/ml anti-Lewis Y with agitation as well as when placed under conditions of fast freezing.

Anti-CD22/Freeze/Thaw

To further investigate the effects of freeze-thaw cycles, anti-CD22 at a concentration of either 1 mg/ml or 25 mg/ml in 20 mM succinate, pH 6.0 and, optionally, containing polysorbate 80 (0.001%), was subjected to various freeze-thaw regimens and zero, one, five, or 10 cycles of the regimen. The regimens were fast freeze/fast thaw (FF/FT), fast freeze/slow thaw (FF/ST), slow freeze/fast thaw (SF/FT), and slow freeze/slow thaw (SF/ST). The percentage of HMV species was then assayed.

Figure 16B:
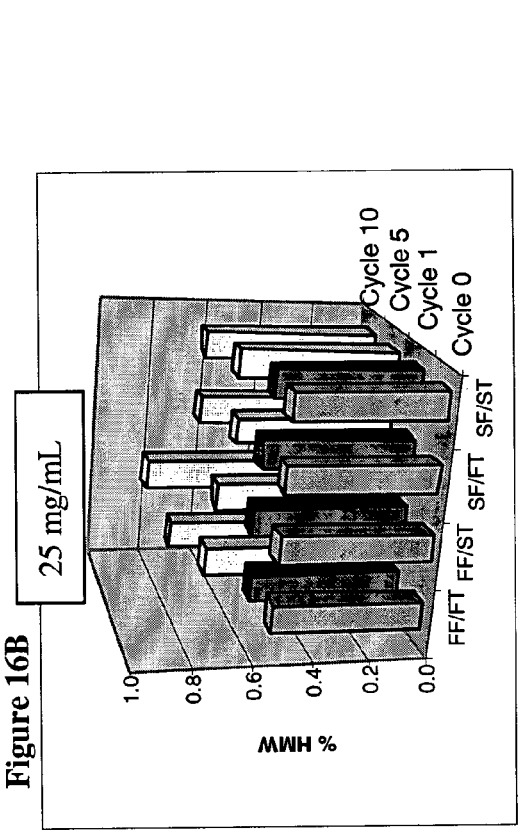
FIG. 16B is a bar graph depicting the results of SEC-HPLC analysis of anti-CD22 at 25 mg/ml in 20 mM succinate, pH 6.0 and treated under various freeze-thaw regimens for various cycles. FF is fast freeze, FT is fast thaw, SF is slow freeze, and ST is slow thaw. Results are expressed as percent HMW species.
Figure 16D:
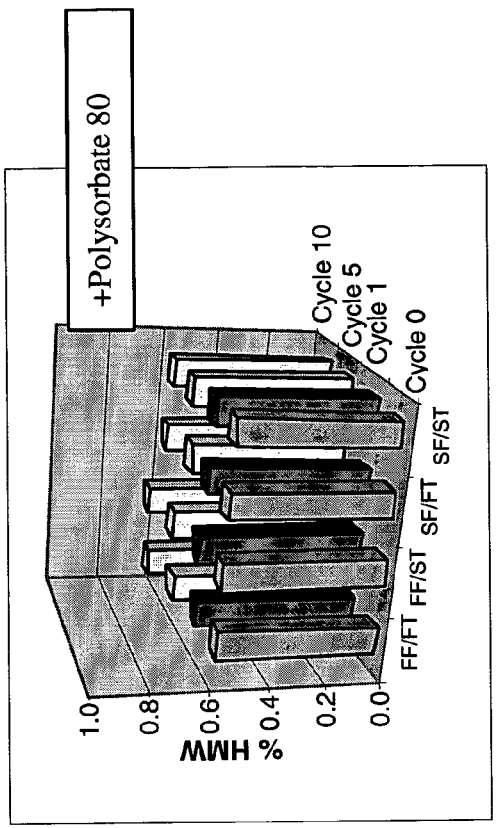
FIG. 16D is a bar graph depicting the results of SEC-HPLC analysis of anti-CD22 at 25 mg/ml in 20 mM succinate, pH 6.0 containing polysorbate 80 and treated under various freeze-thaw regimens for various cycles. FF is fast freeze, FT is fast thaw, SF is slow freeze, and ST is slow thaw. Results are expressed as percent HMW species.
Figure 16A:
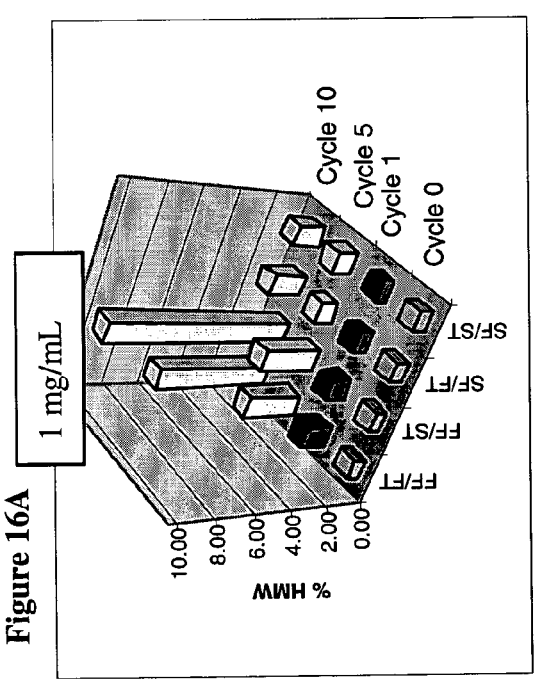
FIG. 16A is a bar graph depicting the results of SEC-HPLC analysis of anti-CD22 at 1 mg/mi in 20 mM succinate, pH 6.0 and treated under various freeze-thaw regimens for various cycles. FF is fast freeze, FT is fast thaw, SF is slow freeze, and ST is slow thaw. Results are expressed as percent HMW species.
Figure 16C:
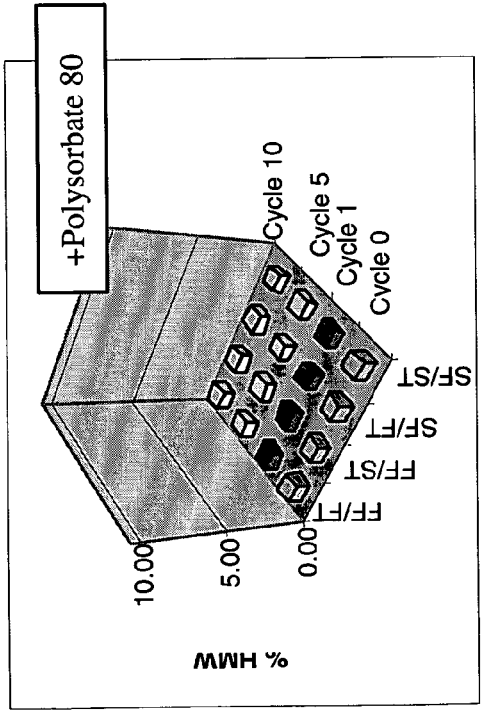
FIG. 16C is a bar graph depicting the results of SEC-HPLC analysis of anti-CD22 at 1 mg/ml in 20 mM succinate, pH 6.0 containing polysorbate 80 and treated under various freeze-thaw regimens for various cycles. FF is fast freeze, FT is fast thaw, SF is slow freeze, and ST is slow thaw. Results are expressed as percent HMW species.

These data demonstrate that at 25 mg/ml, anti-CD22 is not sensitive to freeze/thaw stress, regardless of the presence of polysorbate 80 (FIG. 16B and FIG. 16D). However, at a concentration of 1 mg/ml, anti-CD22 is sensitive to fast freezing (FIG. 16A and FIG. 16C). Thus, for this antibody, if the sample is to be subjected to freeze-thaw cycles, a higher storage concentration should be selected although it is not necessary to include a surfactant.

Storage Stability

FIGS. 5 and 6, show the results of experiments demonstrating that anti-CD22 is stable at –80° C. to 5° C. at 0.5 mg/ml and at 30 mg/ml. At 40° C., the percentage of high molecular weight species increased in sample containing the higher protein concentration after two weeks of storage (FIG. 6), while no change in the percentage of high molecular weight species was detected in samples containing low protein concentrations (FIG. 5).

Example 5

Surfactant Effects

Many protocols for storing protein samples call for the inclusion of a surfactant. The necessity for including surfactant in a storage formulation was therefore investigated. In these experiments, anti-Lewis Y antibody at a concentration of 1 mg/ml or 30 mg/ml in a buffer of 10 mM Na citrate and, optionally, containing 0%, 0.001%, 0.005%, or 0.01% polysorbate 80, were incubated with shaking at 360 rpm at room temperature for 24 hours. The percentage monomer recovery was then assayed using SEC-HPLC.

Figure 17A:
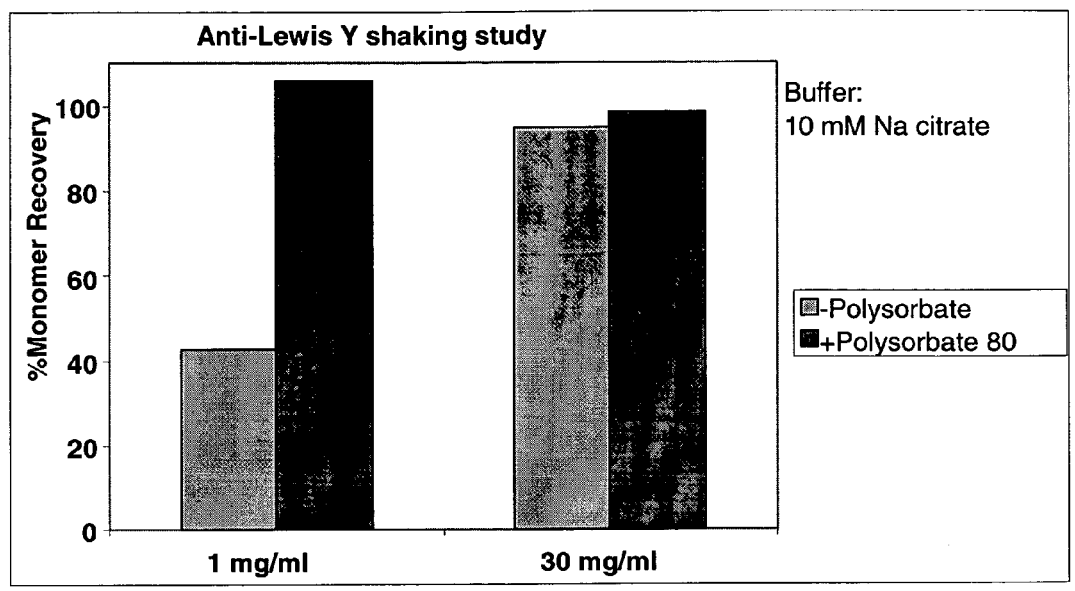
FIG. 17A is a bar graph depicting the results of shaking studies, analyzed using SEC-HPLC, in which 1 mg/ml or 30 mg/ml anti-Lewis Y in 10 mM Na citrate, pH 5.5 in the presence or absence of polysorbate 80 were shaken at 360 rpm for 24 hours at room temperature. Results are expressed as percent monomer recovery.
Figure 17B:
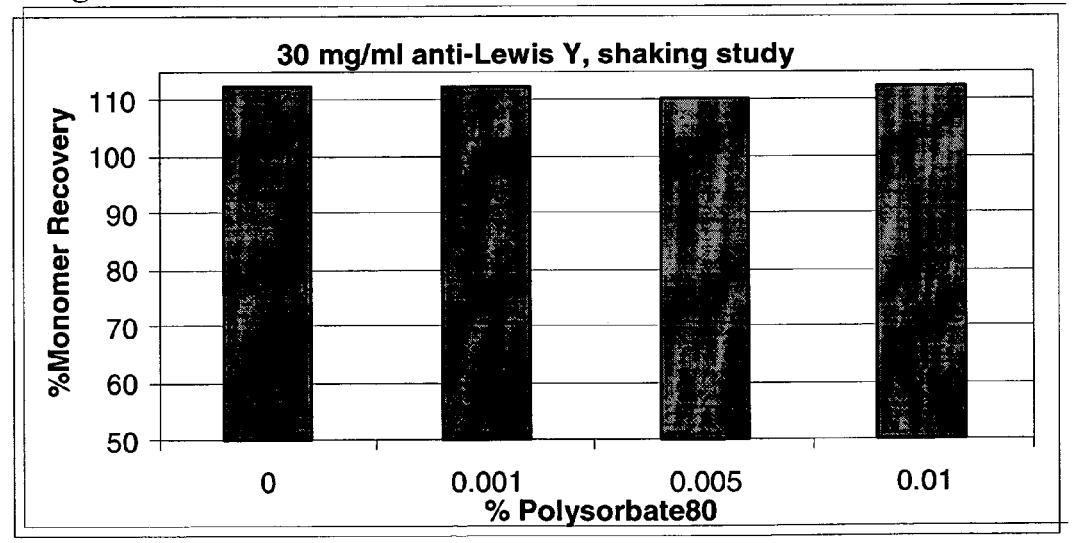
FIG. 17B is a bar graph depicting the results of shaking studies, analyzed using SEC-HPLC, in which 30 mg/ml anti-Lewis Y in 10 mM sodium citrate, pH 5.5 in various concentrations of polysorbate 80 were shaken at 360 rpm for 24 hours at room temperature. Results are expressed as percent monomer recovery.

The data demonstrated that polysorbate 80 is not required when the protein in the formulation is present at a relatively high concentration of 30 mg/ml. At 1 mg/ml, polysorbate 80 did provide some protection of the anti-Lewis Y against agitation stress (FIG. 17A and FIG. 17B).

Freeze/Thaw Stability

The effect of polysorbate 80 on anti-Lewis Y stability during various freeze/thaw conditions was examined. In these experiments, samples were prepared containing either 1 mg/ml or 30 mg/ml anti-Lewis Y antibody in 10 mM Na citrate, pH 5.5, and containing either no polysorbate 80 or 0.01% polysorbate 80. Samples were then subjected to 10 cycles of freeze/thaw as described above.

Figure 18A:
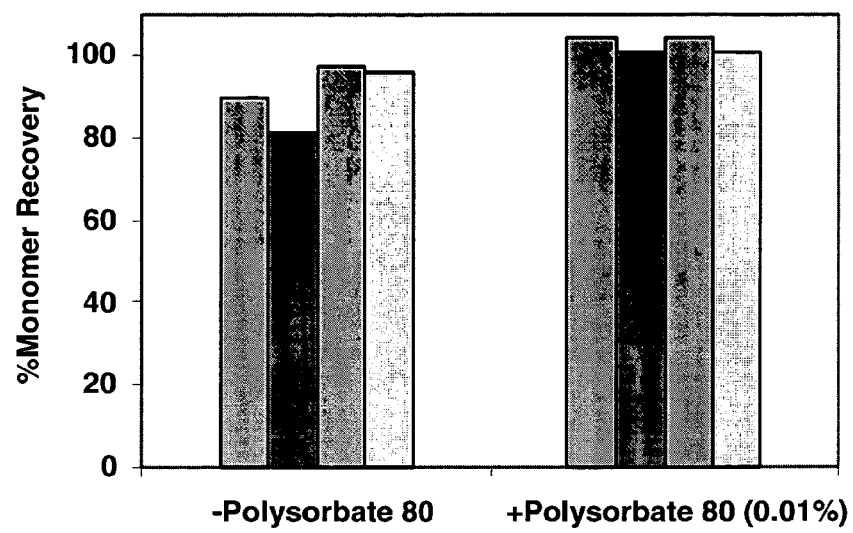
FIG. 18A is a bar graph depicting the results of SEC-HPLC analysis of anti-Lewis Y at 1 mg/ml in 10 mM Na citrate, pH 5.5 in the presence or absence of 0.01% polysorbate 80 following ten freeze thaw cycles as indicated in FIG. 18B. Results are expressed as percent monomer recovery.
Figure 18B:
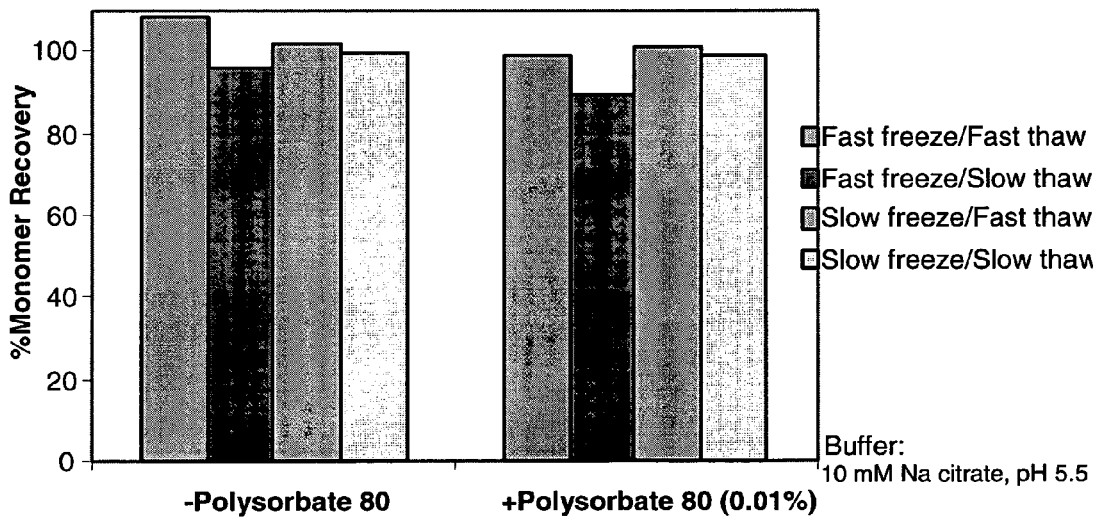
FIG. 18B is a bar graph depicting the results of SEC-HPLC analysis of anti-Lewis Y at 30 mg/ml in 10 mM Na citrate, pH 5.5 in the presence or absence of 0.01% polysorbate 80 following ten freeze thaw cycles as indicated. Results are expressed as percent monomer recovery.

At 30 mg/ml, anti-Lewis Y was not sensitive to freeze/thaw stress regardless of the presence of surfactant (FIG. 18B). Anti-Lewis Y was also stable under slow freezing conditions regardless of protein concentration or thaw conditions (FIG. 18A and FIG. 18B). Polysorbate 80 did not affect the results at 30 mg/ml protein concentration or if slow freezing was used. In samples containing 1 mg/ml antibody, polysorbate 80 protected anti-Lewis Y under fast freezing conditions (FIG. 18A).

Storage Stability

The effect of surfactant on the storage stability of anti-Lewis Y was investigated. In these experiments, samples were prepared containing 30 mg/ml anti-Lewis Y in 10 mM Na citrate, pH 5.5 and 75 mM NaCl. In addition, samples either had 0.001% polysorbate 80 or no polysorbate 80. Samples were incubated at −80° C., −20° C., 5° C., 25° C., or 40° C. for one month, two months, three months, six months, or nine months and the percentage high molecular weight species, percentage low molecular weight species, and percent acidic species were assayed as described herein.

Figure 19A:
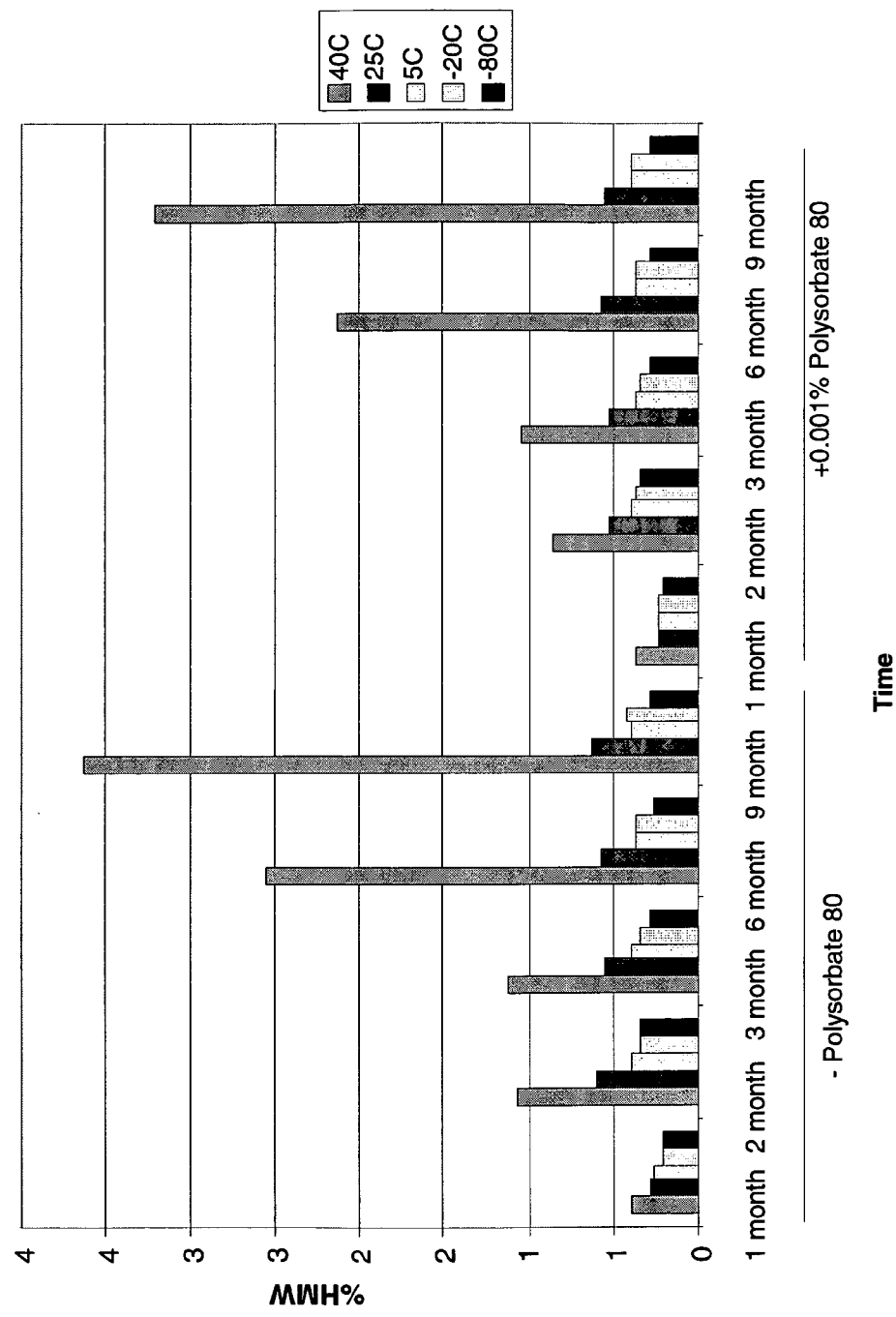
FIG. 19A is a bar graph depicting the results of SEC-HPLC analysis of 30 mg/ml anti-Lewis Y in 10 mM Na citrate, pH 5.5 and 75 mM NaCl in the presence or absence of polysorbate 80 after incubation at various temperatures and for various times. Results are expressed as percent HMW species.
Figure 19B:
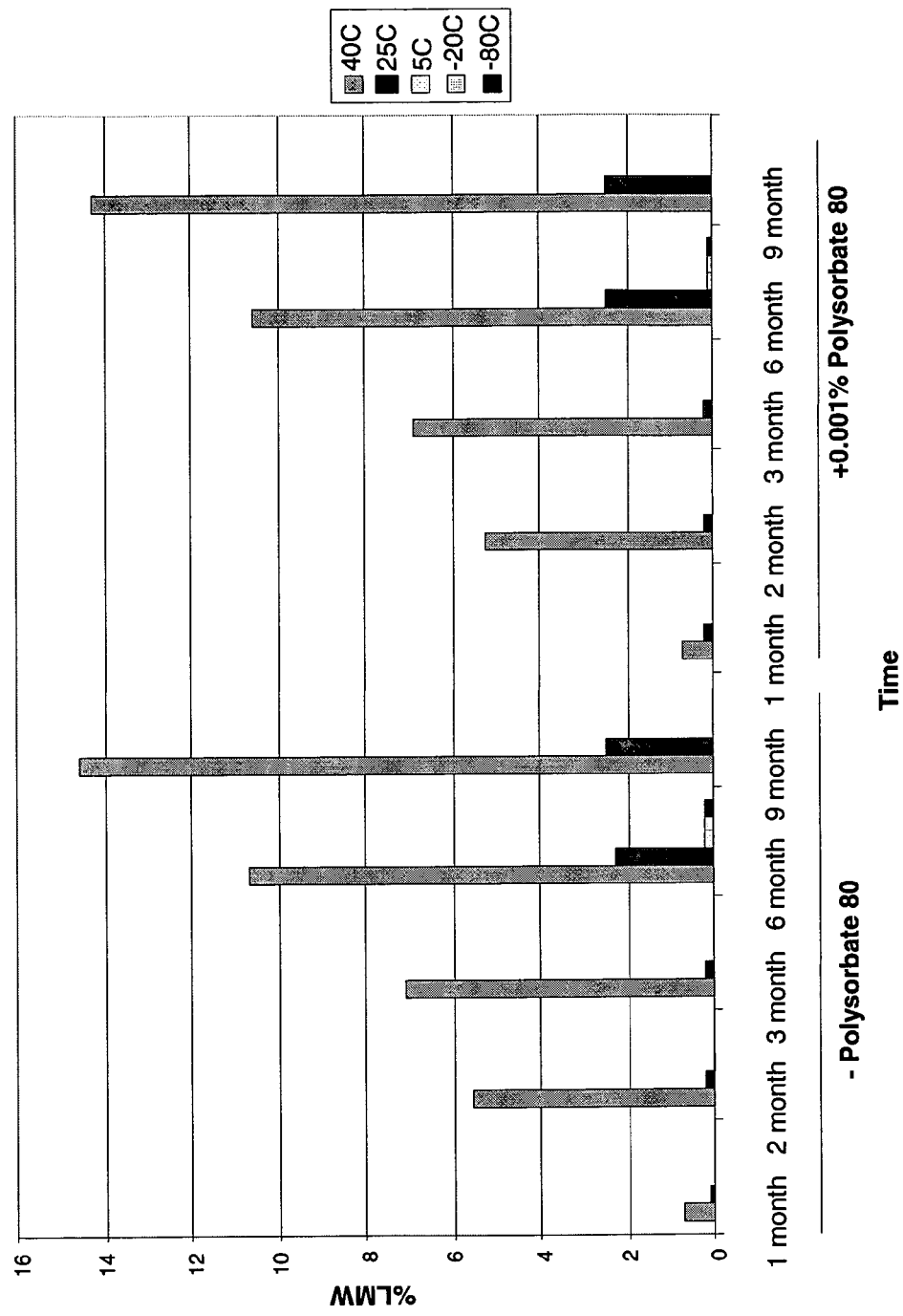
FIG. 19B is a bar graph depicting the results of SEC-HPLC analysis of 30 mg/ml anti-Lewis Y in 10 mM Na citrate, pH 5.5 and 75 mM NaCl in the presence or absence of polysorbate 80 after incubation at various temperatures and for various times. Results are expressed as percent LMW species.
Figure 19C:
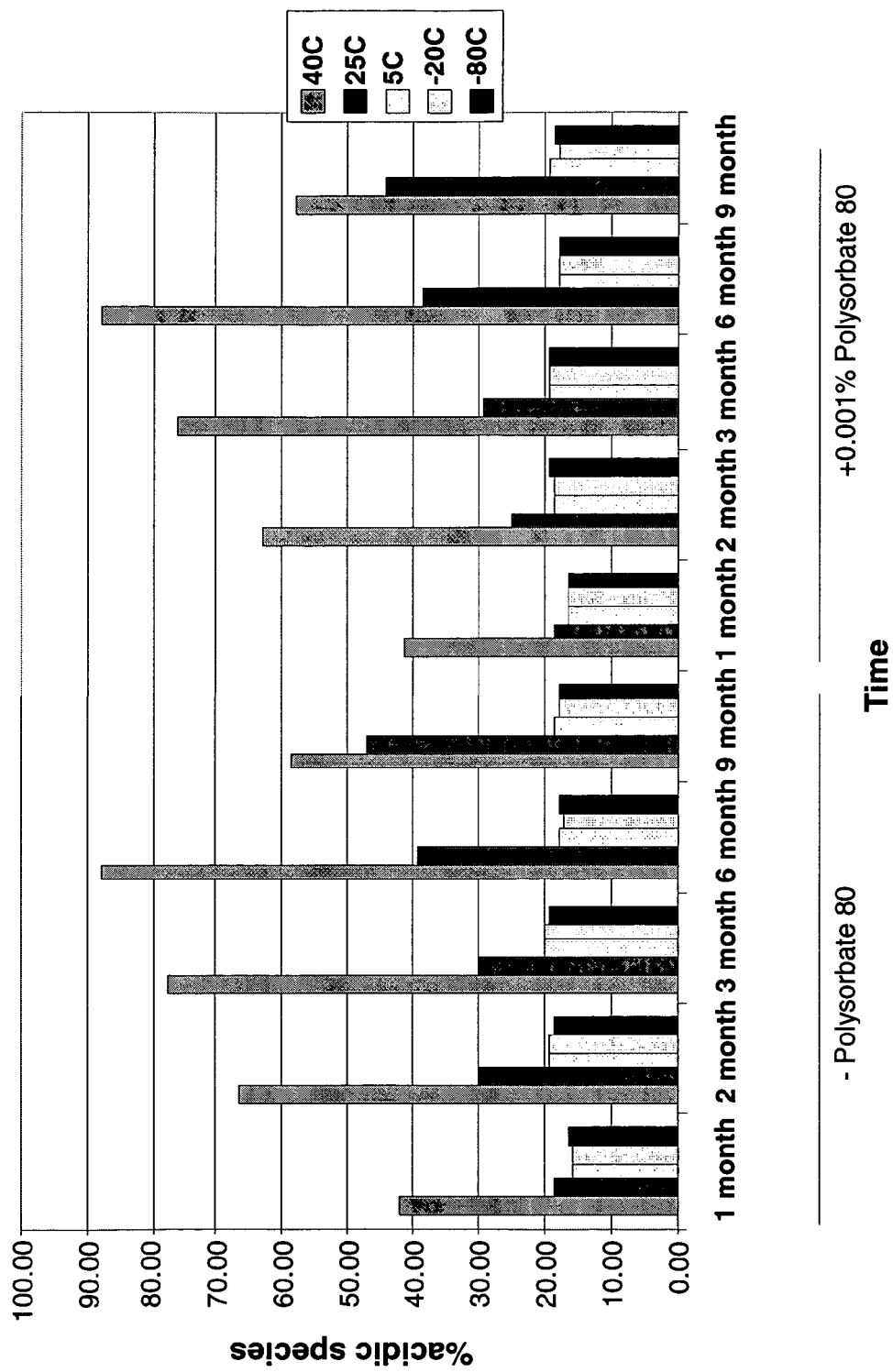
FIG. 19C is a bar graph depicting the results of CEX-HPLC analysis of 30 mg/ml anti-Lewis Y in 10 mM Na citrate, 75 mM NaCl, pH 5.5 in the presence or absence of polysorbate 80 after incubation at various temperatures and for various times. Results are expressed as percent acidic species.

In general, these experiments demonstrated that polysorbate 80 had no significant effect on anti-Lewis Y stability under the test conditions over the complete range of temperatures, −80° C. to 40° C. (FIGS. 19A, 19B, and 19C).

Overall, the results of experiments with anti-Lewis Y demonstrate that at a concentration of 30 mg/ml, anti-Lewis Y is stable under conditions of agitation and freeze/thaw stress conditions. Surfactant is not needed to effect this stability. At a concentration of 1 mg/ml, anti-Lewis is stable under slow freezing conditions. Surfactant is not necessary to effect this condition. Furthermore, at an antibody concentration of 1 mg/ml, polysorbate 80 protects anti-Lewis Y against both agitation and fast freezing induced denaturation and, in general, surfactant has no significant effect on protein stability during storage.

In contrast to the results with anti-Lewis Y, polysorbate 80 is not entirely protective to anti-CD22 against shaking stress (FIG. 13). However, as indicated in the data of FIG. 16, at 25 mg/ml, anti-CD22 is stable under freeze/thaw stress and no surfactant is needed. At 1 mg/ml, anti-CD22 is stable under slow freeze conditions and no surfactant is needed. Surfactant provided additional protection to anti-CD22 only under conditions of fast freezing.

To further investigate the effects of surfactant on anti-CD22, a six month study of anti-CD22 stability was undertaken. In these experiments, anti-CD22 at a concentration of 25 mg/ml was prepared in 20 mM succinate, pH 6.0 (S); 20 mM succinate, 10 mM methionine, pH 6.0 (SM); 20 mM succinate, 0.01% polysorbate 80, pH 6.0 (ST); or 20 mM succinate, 10 mM methionine, 0.01% polysorbate 80, pH 6.0 (SMT); and incubated for six months at −80° C., 2-8° C., 25° C., or 40° C. Samples were then assayed for the percentage high molecular weight species, percentage total peak area (which is an indication of recovery), and percent fully active species. Note that peak 5 is the fully active species.

Figure 20A:
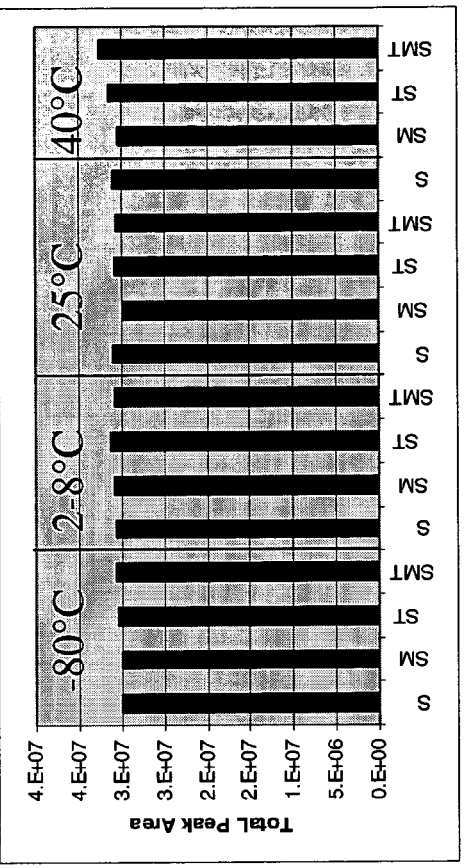
FIG. 20A is a bar graph depicting the results of SEC-HPLC analysis of storage stability of anti-CD22 for six months. Solutions contain 20 mM succinate, pH 6.0 (S); 20 mM succinate, 10 mM methionine, pH 6.0 (SM); 20 mM succinate, 0.01 polysorbate 80, pH 6.0 (ST); or 20 mM succinate, 10 mM methionine, 0.01 polysorbate 80, pH 6.0 (SMT). Results are expressed as percent HMW species.
Figure 20B:
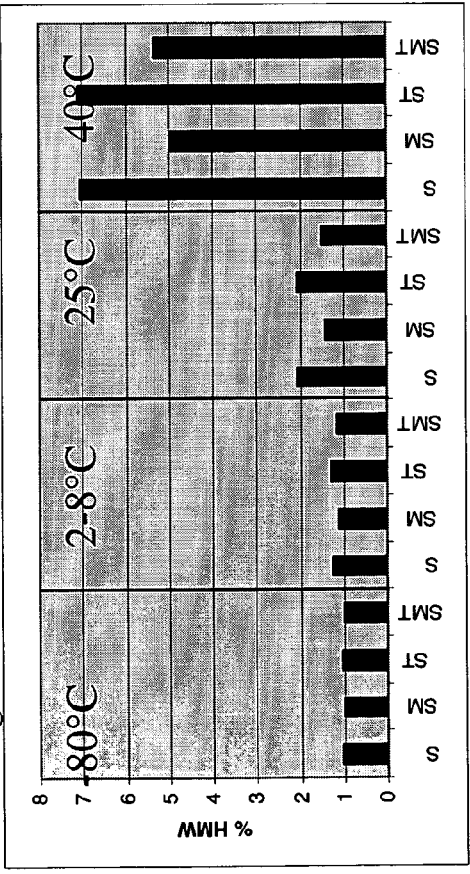
FIG. 20B is a bar graph depicting the results of SEC-HPLC analysis of storage stability of anti-CD22 for six months. Solutions contain 20 mM succinate, pH 6.0 (S); 20 mM succinate, 10 mM methionine, pH 6.0 (SM); 20 mM succinate, 0.01 polysorbate 80, pH 6.0 (ST); or 20 mM succinate, 10 mM methionine, 0.01 polysorbate 80, pH 6.0 (SMT). Results are expressed as percent total peak area.
Figure 20C:
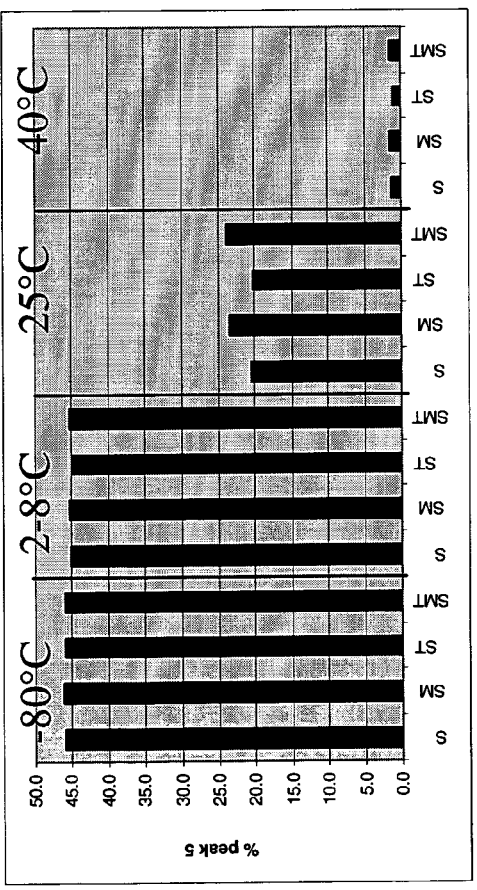
FIG. 20C is a bar graph depicting the results of CEX-HPLC analysis of storage stability of anti-CD22. Conditions are as described in FIG. 20A and 20B. Results are expressed as percent fully active species (% peak 5).

In general, none of the parameters show any significant effect on stability of anti-CD22 (FIG. 20A, FIG. 20B, and FIG. 20C).

Overall, both the short-term storage data and long-term storage data for two different antibodies (an anti-Lewis Y and an anti-CD22) demonstrate that surfactant (polysorbate 80) is not necessary for stabilization of antibodies in a storage formulation.

Example 6

Formulation for Storage of Anti-5T4

As another example of determining a formulation for storage of a protein, parameters of salt concentration, pH, protein concentration and buffer type and concentration were evaluated for storage of an antibody directed against 5T4.

pH

Figure 21:
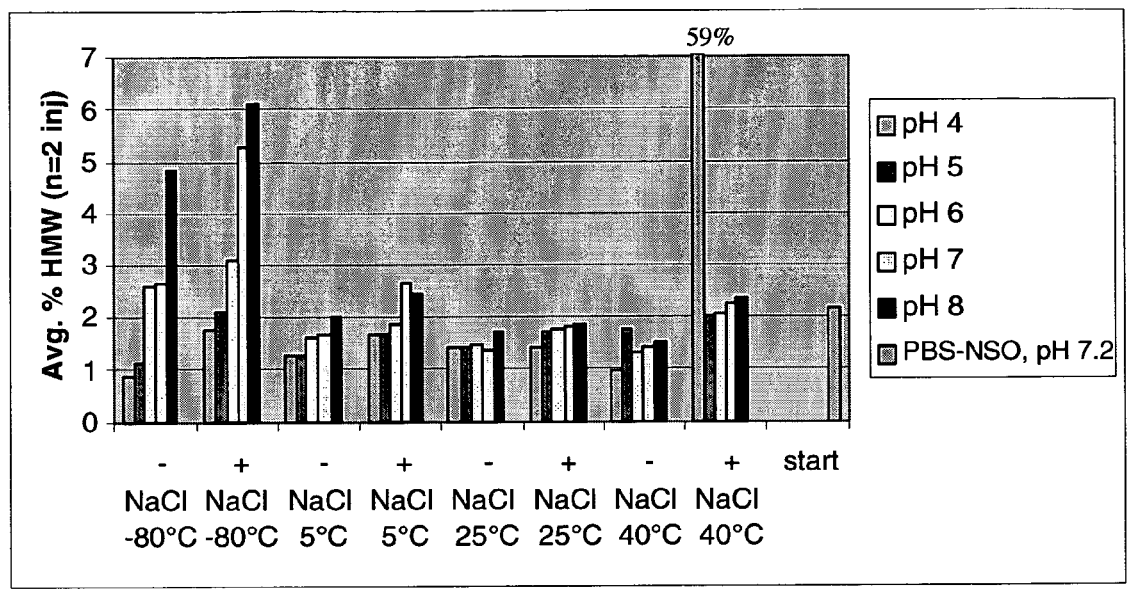
FIG. 21 is a bar graph depicting the results of SEC-HPLC analysis of the high molecular weight products (HMW) of anti-5T4 stored at various pHs and temperatures for two weeks. Results are expressed as average percent high molecular weight products.

To identify an advantageous pH to be used in a formulation for storage of an anti-5T4 antibody, samples containing 1 mg/ml anti-5T4 were tested at a pH range from pH 4.0 to pH 8.0. The samples were prepared by dialysis into each pH buffer. All formulations used in these experiments employed a 10 mM sodium phosphate buffer with or without 150 mM NaCl. The protein in a formulation was sterile filtered and placed in a −80° C. freezer, or in a stability chamber maintained at 5° C., 25° C., or 40° C. Samples were then assayed for the presence of high molecular weight species (HMW) (FIG. 21).

Anti-5T4 was found to have the lowest amount of high molecular weight species in the absence of NaCl at 5° C., 25° C., and 40° C. over the entire pH range when in 10 mM sodium phosphate buffer. The antibody was not stable to a freeze/thaw cycle at pH 7 in a formulation containing NaCl and at pH 8 with sodium phosphate as the buffer. The protein was also observed to be unstable at pH 4 with 150 mM NaCl at 40° C.

Isoelectric focusing (IEF) was performed on samples prepared and stored at the various pHs (as described above) and stored at 40° C. for two weeks. It was found that samples stored in a formulation at pH 4 (without NaCl) and at pH 5 and pH 6 (with or without NaCl) displayed the least amount of change in overall protein charge.

SDS-PAGE analysis of anti-5T4 pH screen samples stored at 40° C. for two weeks was also performed. Samples in the pH range of pH 5.0 to pH 7.0 displayed least amount of high molecular weight species in the non-reduced gel and the least amount of change in protein molecular weight compared to starting material in a reduced gel.

These data demonstrate that the anti-5T4 is stable in 10 mM sodium phosphate in the presence or absence of NaCl at −80° C., 5° C., and 25° C. over the pH range of pH 4.0 to pH 7.0. Based on accelerated results (i.e., results obtained at higher temperatures) of the pH screen, pH 5 to pH 6 is selected as the advantageous pH range for anti-5T4 stability.

Buffers

Four different buffer systems were tested for stable storage of anti-5T4 in formulations in the pH range from 5.0 to 7.0. The effect of ionic strength on stability was also evaluated. These buffer systems used were 10 mM sodium acetate, pH 5.0; 10 mM sodium acetate 5.5; 10 mM sodium acetate, 150 mM NaCl, pH 5.0; 10 mM sodium acetate, 150 mM NaCl, pH 5.5; 10 mM sodium citrate, pH 5.0; 10 mM sodium citrate pH 5.5, 10 mM sodium citrate, pH 6.0; 10 mM sodium citrate, 150 mM NaCl, pH 5.0; 10 mM sodium citrate, 150 mM NaCl, pH 5.5; 10 mM sodium citrate, 150 mM NaCl, pH 6.0; 10 mM sodium phosphate, pH 6.0; 10 mM sodium phosphate, pH 6.5; 10 mM sodium phosphate, pH 7.0; 10 mM sodium phosphate, 150 mM NaCl, pH 6.0; 10 mM sodium phosphate, 150 mM NaCl, pH 6.5; 10 mM sodium phosphate, 150 mM NaCl, pH 7.0; 10 mM sodium succinate, pH 5.0; 10 mM sodium succinate, 5.5; 10 mM sodium succinate, pH 6.0; 10 mM sodium succinate, pH 6.5; 10 mM sodium succinate, 150 mM NaCl, pH 5.0; 10 mM sodium succinate, 150 mM NaCl, pH 5.5; 10 mM sodium succinate, 150 mM NaCl, pH 6.0; and 10 mM sodium succinate, 150 mM NaCl, pH 6.5.

Figure 22:
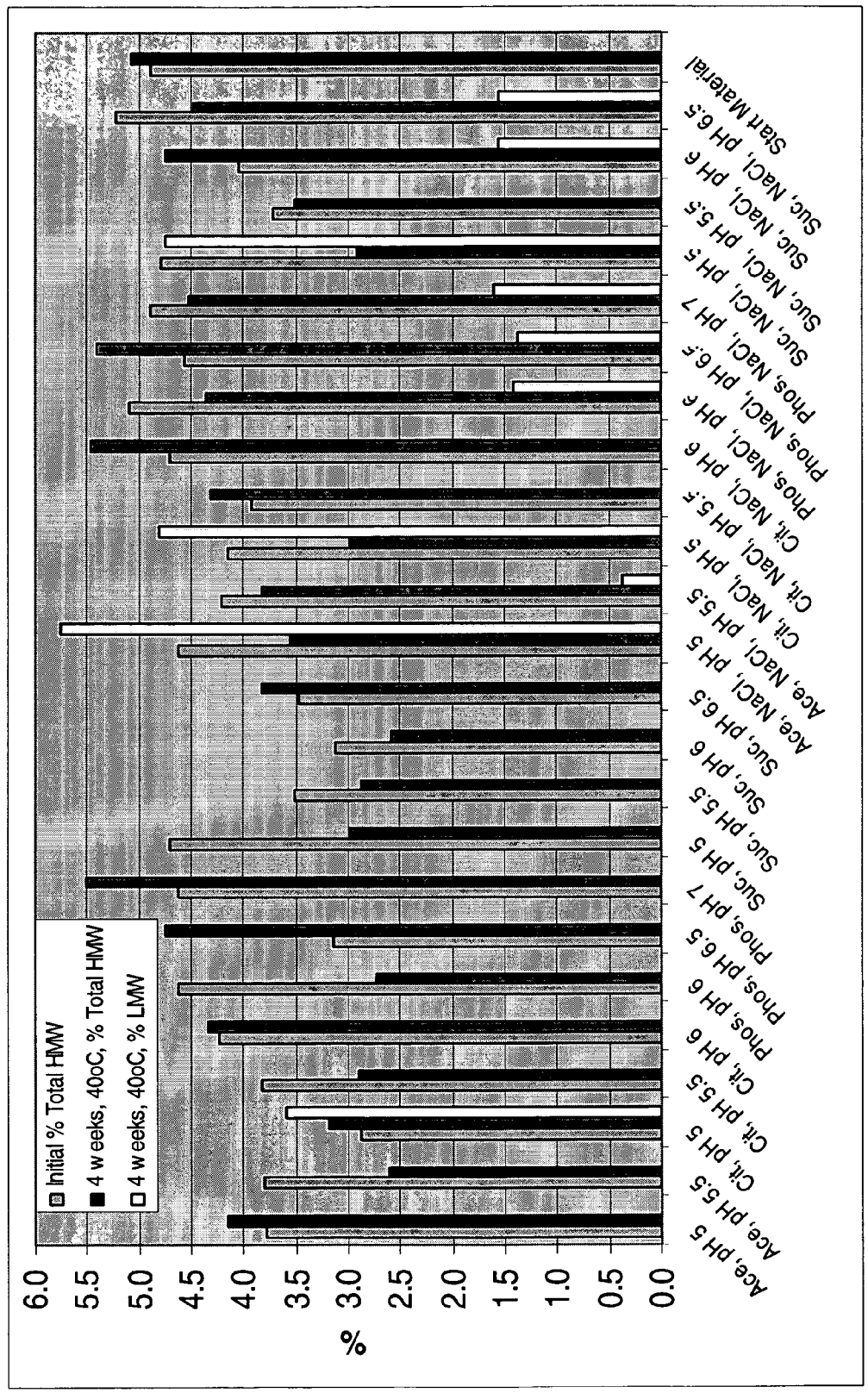
FIG. 22 is a bar graph depicting the results of SEC-HPLC analysis of the percentage of high molecular weight products (HMW) or low molecular weight products (LMW) in anti-5T4 samples initially or after four weeks at 40° C. in acetate buffer (Ace), citrate buffer (Cit), phosphate buffer (Phos), or succinate buffer (Suc), with or without salt (NaCl), at various pHs.

Anti-5T4 was dialyzed into the above buffers and diluted to a final concentration of 2 mg/ml. Samples were stored at −80° C. and 40° C. for up to four weeks, then analyzed using SEC-HPLC of initial samples (before storage) and after storage for four weeks. In these data (FIG. 22), it was found that high molecular weight species were not the major degradation products and the percentage of high molecular weight species in each formulation after four weeks of storage was comparable to, or less than, the percentage of high molecular weight species present in the initial samples. Low molecular weight species were elevated in most of the NaCl-containing formulations.

Figure 23B:
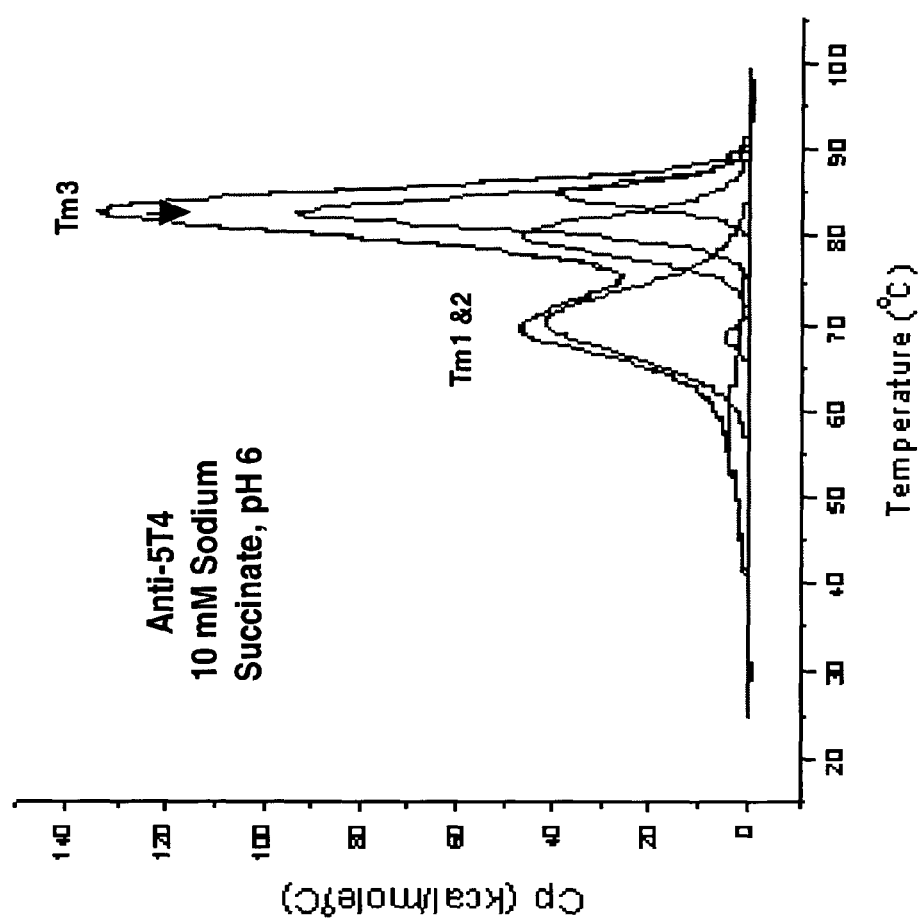
FIG. 23B is a thermogram depicting the results of differential scanning calorimetry (DSC) of anti-5T4 in succinate buffer (pH 6.0).
Figure 23A:
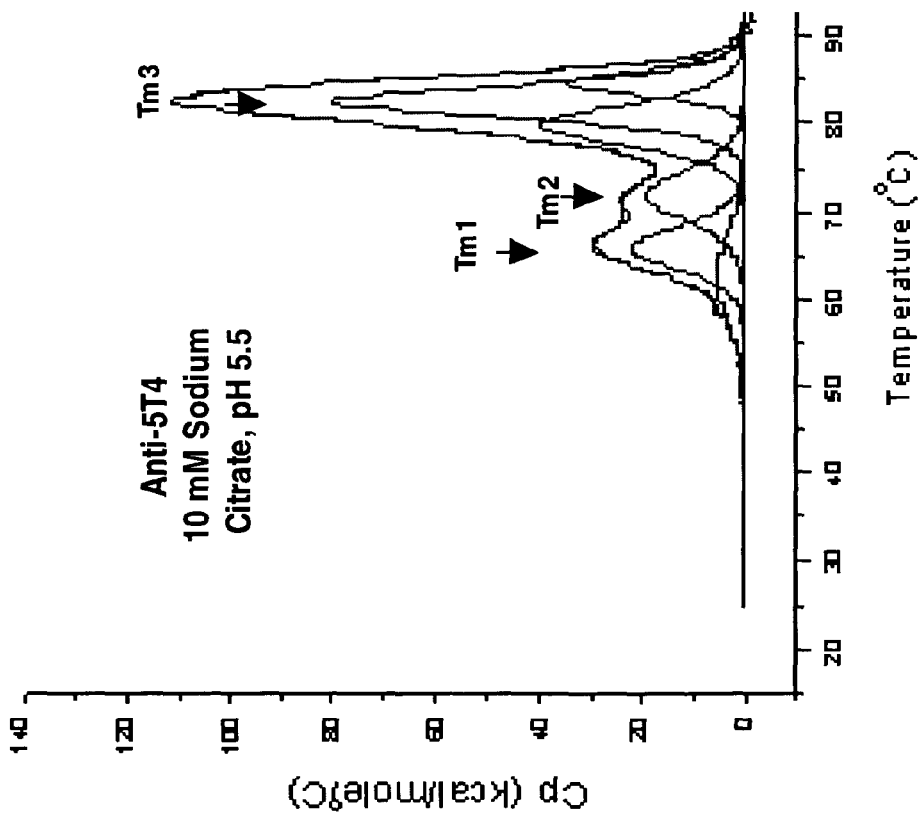
FIG. 23A is a thermogram depicting the results of differential scanning calorimetry (DSC) of anti-5T4 in citrate buffer (pH 5.5).
Figures 24A, 24B:
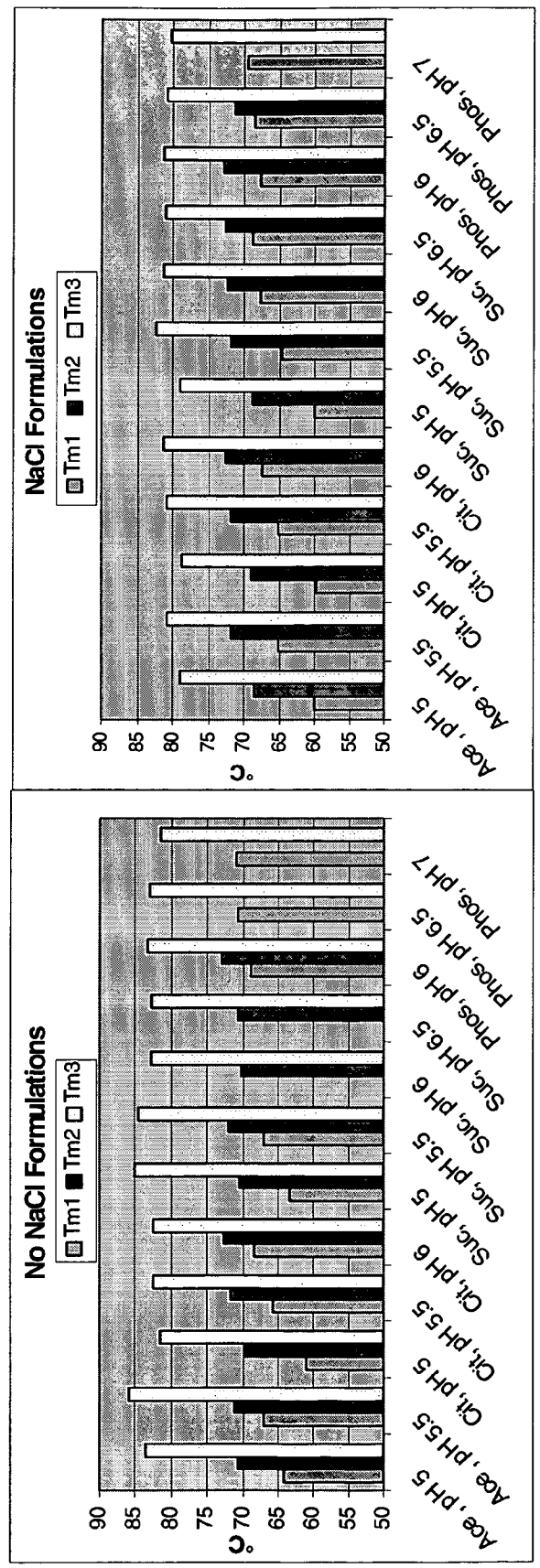
FIG. 24A is a bar graph depicting the results of DSC of anti-5T4 in various formulations, without NaCl, and at various pHs.
FIG. 24B is a bar graph depicting the results of DSC of anti-5T4 in various formulations containing 150 mM NaCl at various pHs.

Thermal melts ($T_m$s) were performed to assess the effect of storage in various formulations on the thermal stability of a protein (anti-5T4). Differential scanning calorimetry (DSC) was used to generate thermograms. Examples of such thermograms are shown in FIG. 23A). The differential scanning calorimetry results are illustrated in FIG. 23B.

Protein in formulations having a pH of 5.0 were the least thermally stable when the formulation used citrate or succinate as the buffer. NaCl was found to be thermally destabilizing since the $T_m$ values were lower at each pH/buffer condition as compared to their corresponding NaCl free formulations. All other formulations in the pH range of 5.5 to 7.0 in acetate, citrate, succinate, and phosphate buffers exhibited the highest $T_m$s and therefore the highest thermal stability.

Figure 25:
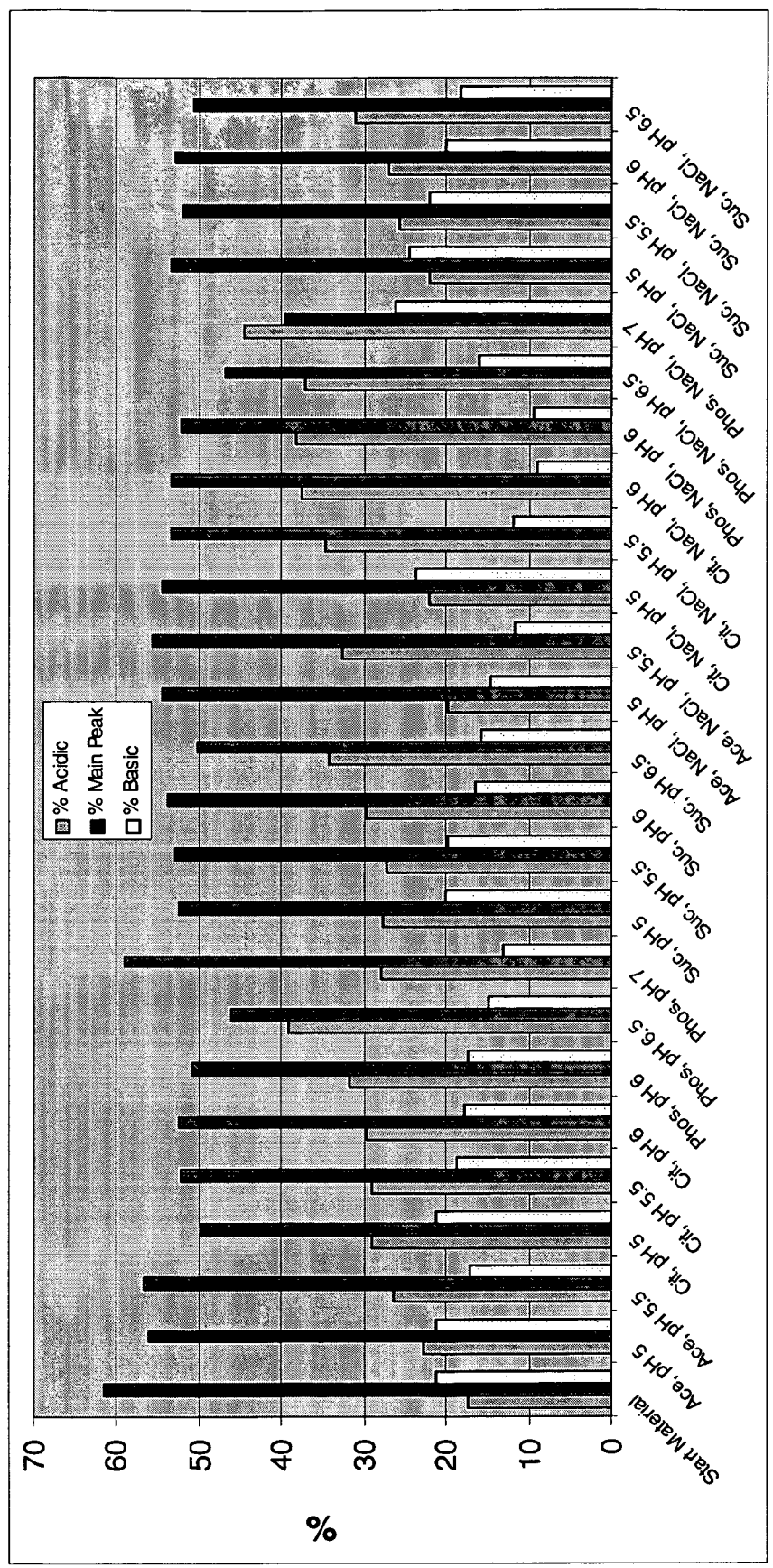
FIG. 25 is a bar graph depicting the results of CEX-HPLC of anti-5T4 in formulations containing various buffers, with or without 150 mM NaCl, at various pHs after four weeks at 40° C.

CEX-HPLC was also used to analyze the stability of anti-5T4. In these studies, CEX-HPLC was performed on samples after storage for four weeks at 40° C. These results are illustrated in FIG. 25 and demonstrate an increase in the percentage of acidic species and a decrease in the percentage of basic species at higher pH for all four tested buffers. Some of the formulations containing NaCl also had higher levels of acidic species and lower levels of basic species than the corresponding NaCl-free formulations.

To further analyze the stability of the various formulations, reducing SDS-PAGE was performed on the samples after storage for four weeks at 40° C. Analysis of these samples demonstrated that samples stored in formulations of pH 5.5 and pH 6.0 retained the least amount of change in protein molecular weight as compared to starting material in the reducing gel.

In general, these data demonstrate that the anti-5T4 protein used in these experiments had similar stability in all four tested buffers (sodium acetate, citrate, phosphate, and succinate) when stored at a pH of pH 5.5-6.5. An accelerated stability study showed that the least amount of low molecular weight species were formed the formulations that did not contain NaCl.

Effect of Salt (NaCl)

As illustrated above, anti-5T4 is stable in 10 mM sodium phosphate in formulations at pH 5-6 at –80° C., 5° C., and 25° C. in 150 mM NaCl. However, NaCl did not improve the stability and therefore provides no stability benefit (FIG. 21).

The results of an accelerated stability study at 40° C. demonstrated that NaCl promotes high molecular weight and low molecular weight formation and lowers the thermal stability of the antibody (FIG. 22, FIG. 24A, FIG. 24B, and FIG. 25).

Antibody Concentration

Figure 26A:
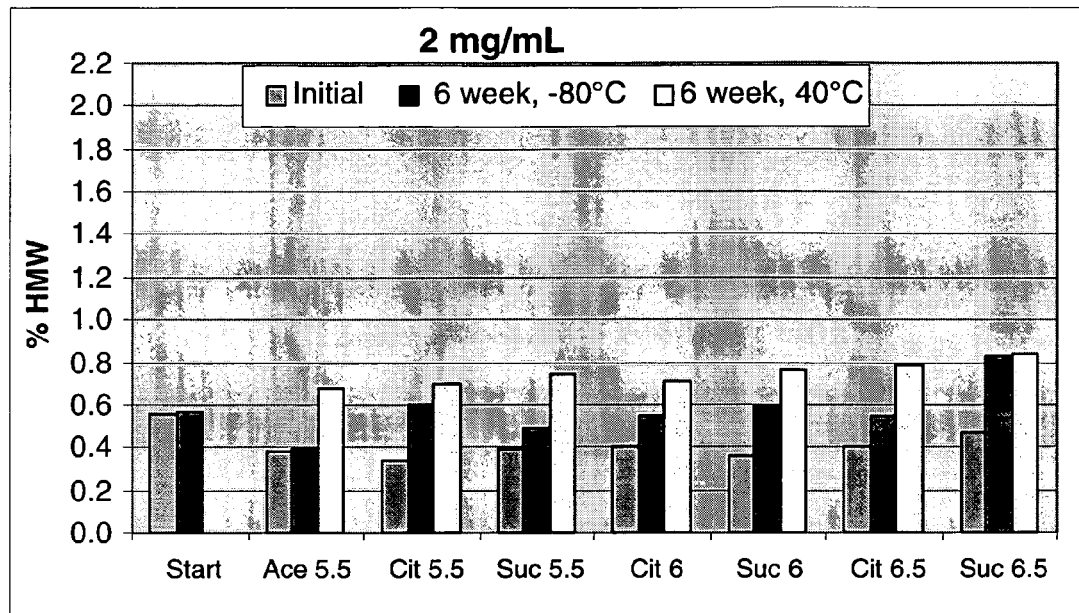
FIG. 26A is a bar graph depicting the results of SEC-HPLC of anti-5T4 (2 mg/ml) in various buffers at various pHs after six weeks at -80° C. or 40° C.
Figure 26B:
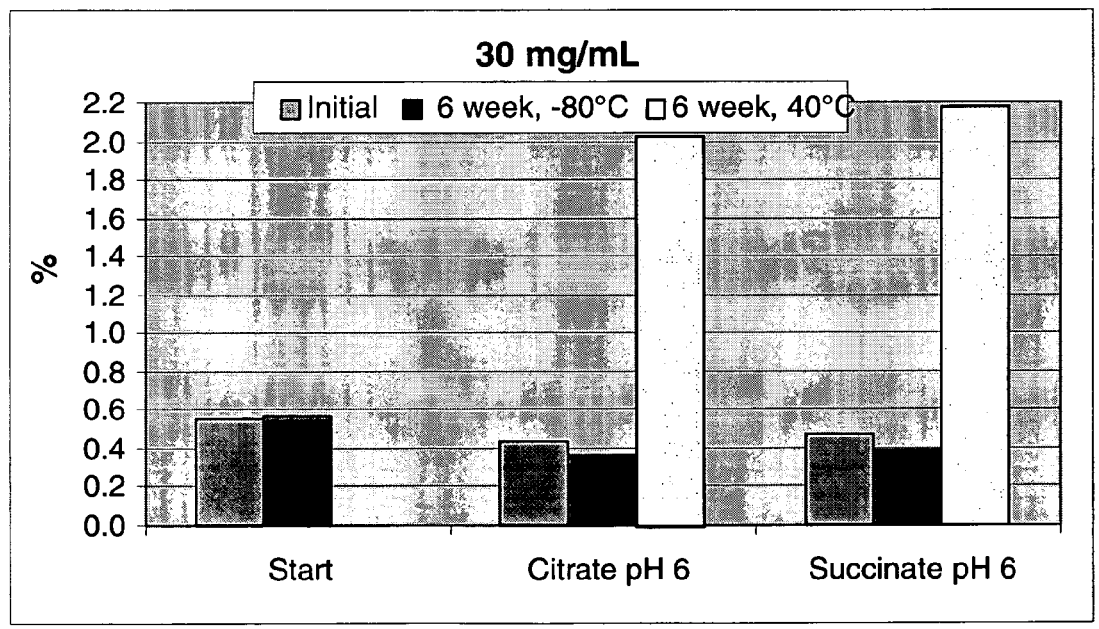
FIG. 26B is a bar graph depicting the results of SEC-HPLC of anti-5T4 (30 mg/ml) in citrate or succinate buffer at pH 6 after six weeks at −80° C. or 40° C.

The effects of antibody (protein) concentration on storage stability were examined. In these experiments, the sodium acetate, sodium citrate, and sodium succinate buffer systems were again tested using a narrow pH range; from 5.5 to 6.5. Anti-5T4 was dialyzed into the buffers and diluted to a final concentration of 2 mg/ml. An additional set of samples was prepared with a concentration of 30 mg/ml in citrate or succinate. Samples were stored at –80° C. and 40° C. for up to six weeks, and then were analyzed. FIG. 26A and FIG. 26B illustrate the results of SEC-HPLC analysis of these samples. In general, these data demonstrate that comparable stability is observed for the 2 mg/ml and 30 mg/ml formulations, although the higher protein concentration accumulated a slightly greater amount of high molecular weight species after six weeks at 40° C.

Figure 27A:
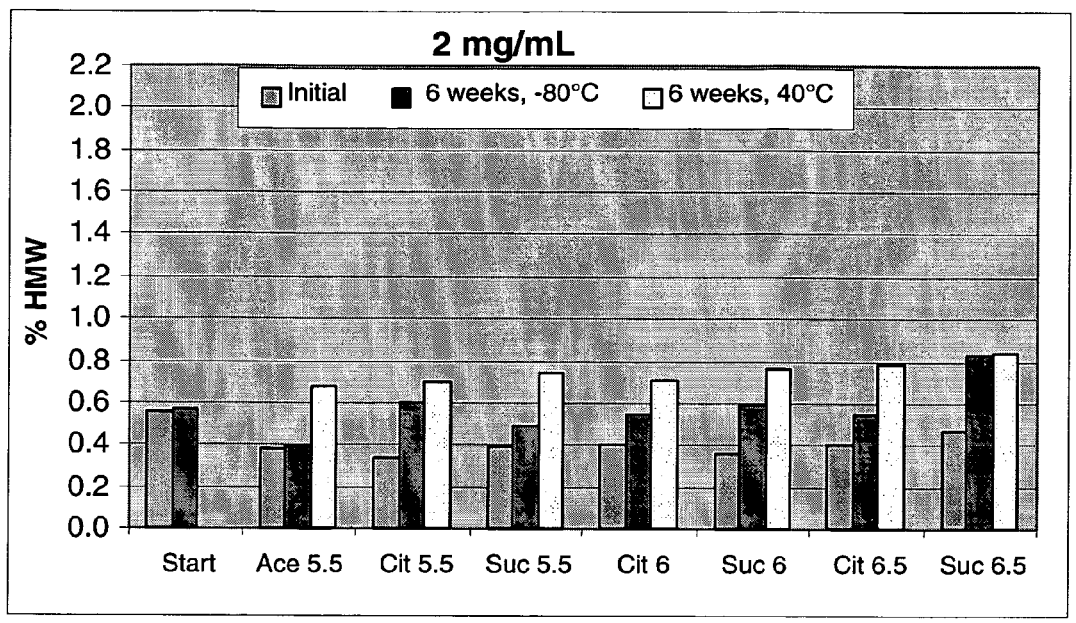
FIG. 27A is a bar graph depicting the results of CEX-HPLC of anti-5T4 (2 mg/ml) in various buffer formulations at various pHs after six weeks at 40° C.
Figure 27B:
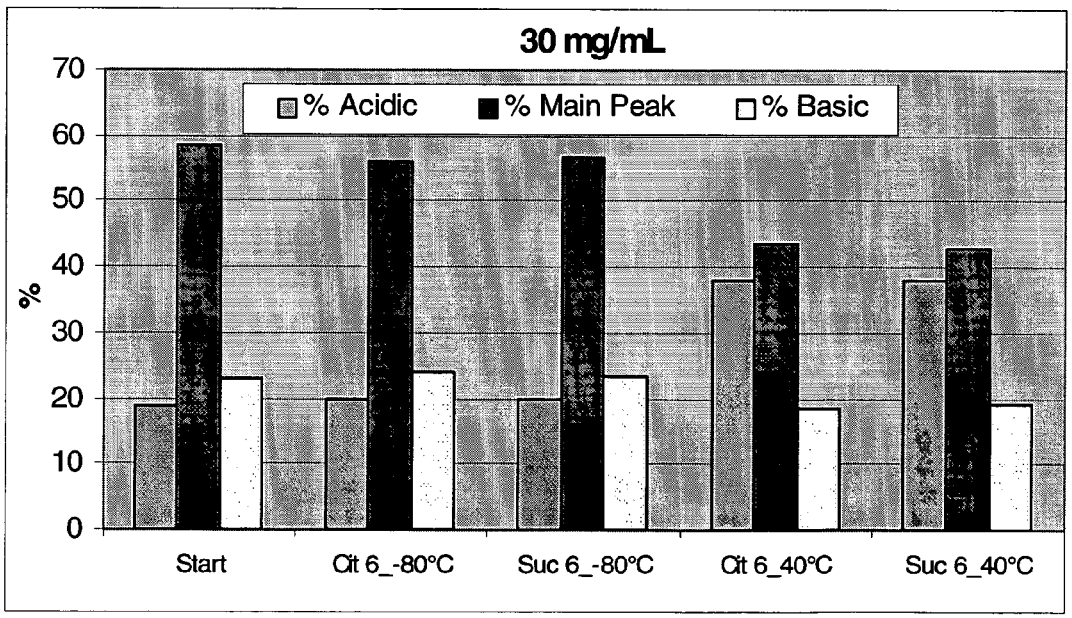
FIG. 27B is a bar graph depicting the results of CEX-HPLC of anti-5T4 (30 mg/ml) in citrate or succinate buffer at pH 6 after six weeks at 40° C.

CEX-HPLC was also performed on these samples after 6 weeks of storage at 40° C. Comparable stability was observed for pH 5.5 formulations containing 2 mg/ml or 30 mg/ml, although the pH 5.5 samples at 2 mg/ml had a slightly lower percentage of acidic species after storage for six weeks at 40° C. (FIGS. 27A and 27B).

Figure 28:
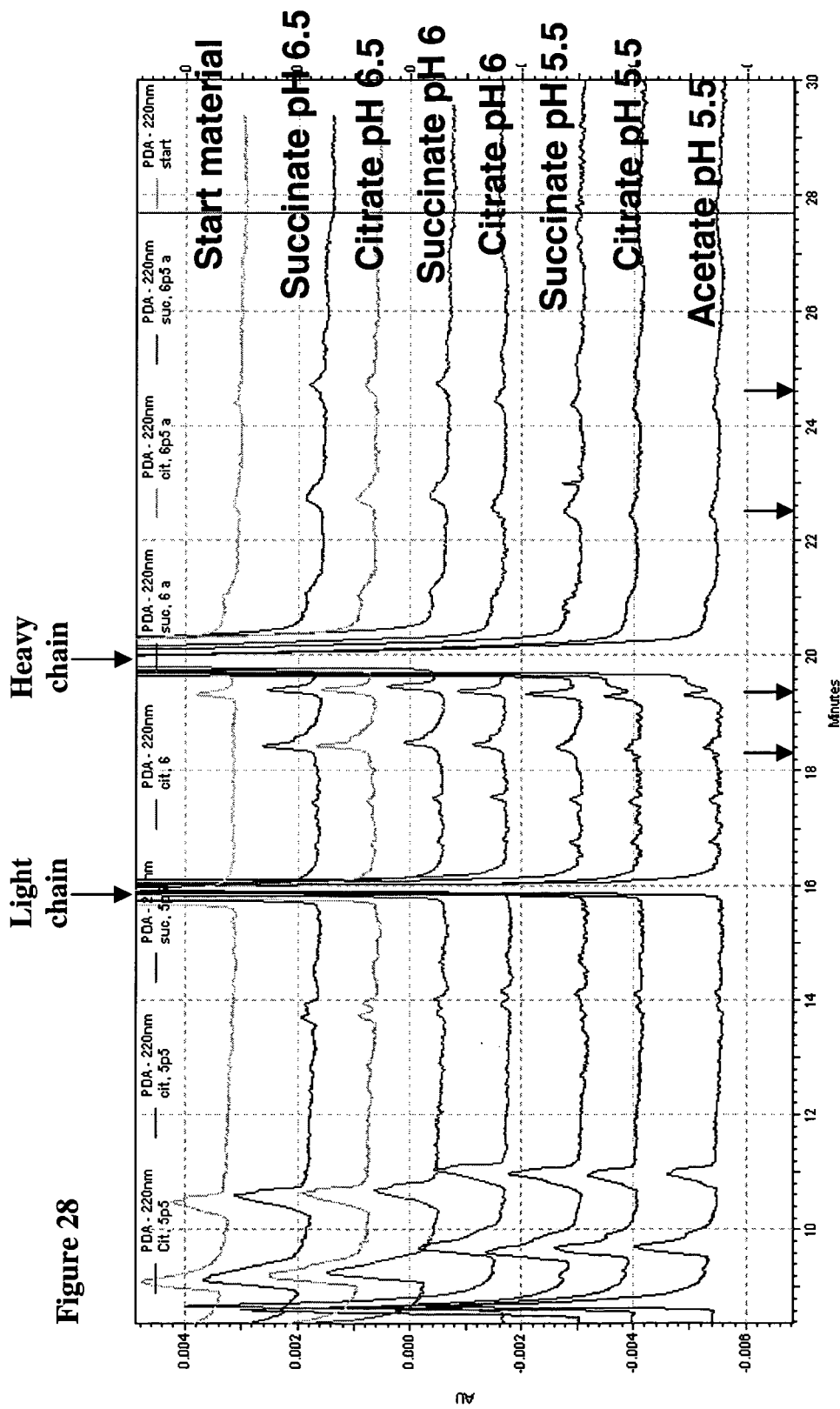
FIG. 28 is a reproduction of a set of overlaid electropherograms depicting the results of capillary electrophoresis in SDS gels of anti-5T4 in various buffer formulations at various pHs after six weeks at 40° C.

Capillary electrophoresis SDS (ceSDS; an SDS-PAGE equivalent method) was also used to analyze the 2 mg/ml samples that were stored for six weeks at 40° C. In these experiments, nearly comparable stability was observed for the 2 mg/ml samples, with the pH 5.5 samples showing slightly less change in protein molecular weight. Comparable stability is observed for 2 mg/ml samples with the pH 5.5 samples showing slightly less change in protein MW by capillary electrophoresis SDS method (SDS-PAGE equivalent method) (FIG. 28).

Freeze/Thaw and Shaking Stability

The sodium acetate, sodium citrate, and sodium succinate buffer systems were tested in a study of protein stability under conditions of freeze/thaw and shaking Study at pH 5.5 in the presence or absence of 0.005% vegetable-derived polysorbate 80 and 3% sucrose. In these experiments, anti-5T4 was dialyzed into the buffers and diluted to final concentrations of 25 mg/ml and 1 mg/ml. Samples were frozen in liquid nitrogen (about –196° C. or at –80° C. and then thawed at 37° C. or at ambient temperature. A separate set of samples was shaken at 200 rpm for 24 hours, at 20° C.

Figure 29A:
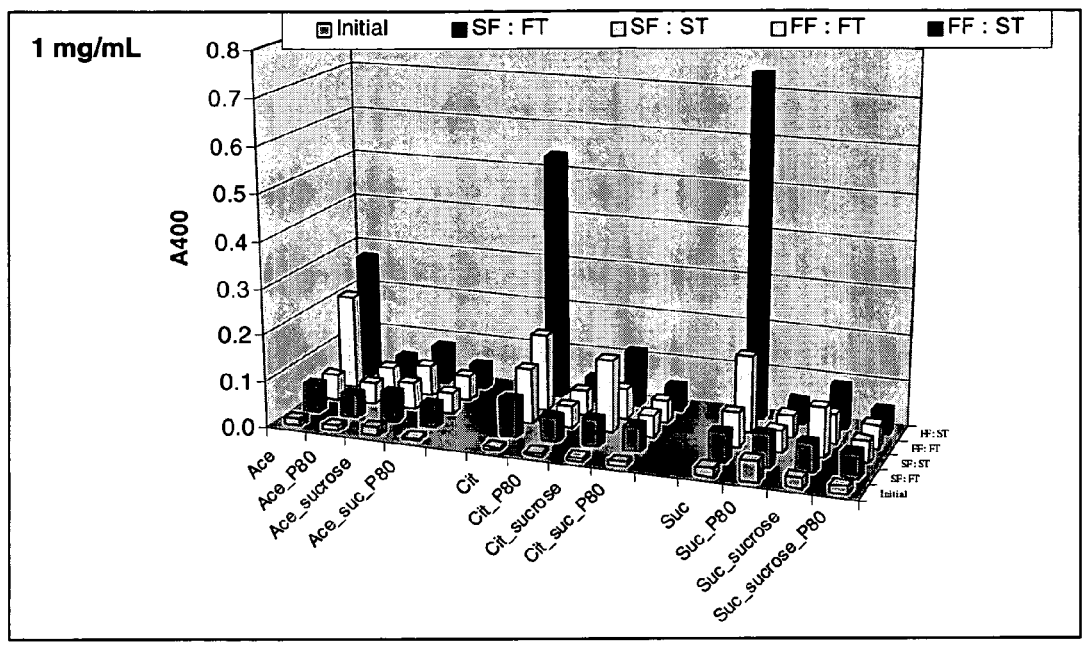
FIG. 29A is a bar graph depicting the $A_{400}$ of anti-5T4 at 1 mg/ml in formulations containing various buffers (pH 5.5) and with or without polysorbate 80 (P80), and with or without sucrose under different freezing and thawing regimens. FF is fast freeze, SF is slow freeze, FT is fast thaw, and ST is slow thaw.
Figure 29B:
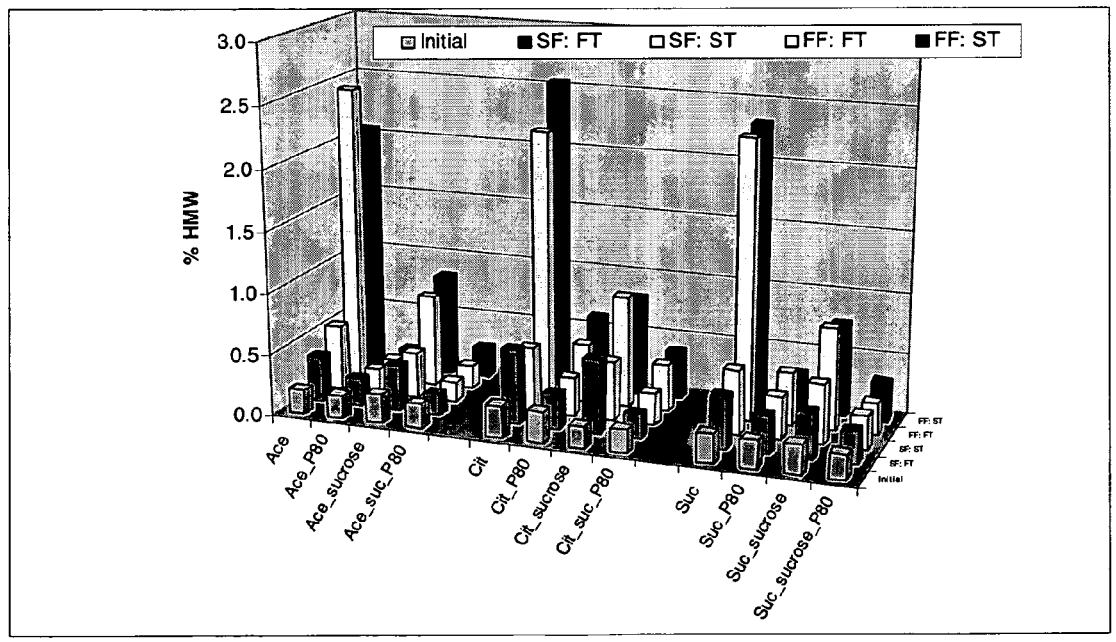
FIG. 29B is a bar graph depicting the percentage of high molecular weight (HMW) species of anti-5T4 at 1 mg/ml in formulations containing various buffers (pH 5.5) and with or without polysorbate 80 (P80), and with or without sucrose under different freezing and thawing regimens. FF is fast freeze, SF is slow freeze, FT is fast thaw, and ST is slow thaw.

Turbidity was assayed after a cycle of freeze/thaw by measuring absorbance at $A_{400}$, and the percentage of high molecular weight species was determined for the 1 mg/ml samples. After one freeze/thaw cycle, anti-5T4 was slightly sensitive to slow freezing (SF) conditions (–80) at 1 mg/ml and very sensitive to faster freezing (FF) conditions (liquid nitrogen). Polysorbate 80 minimized turbidity and the percentage of high molecular weight species was increased in 1 mg/ml samples. Sucrose improved (minimized) turbidity and in the presence of sucrose, the percentage of high molecular weight species increased only under fast freeze conditions (FIG. 29A and FIG. 29B).

Figure 30A:
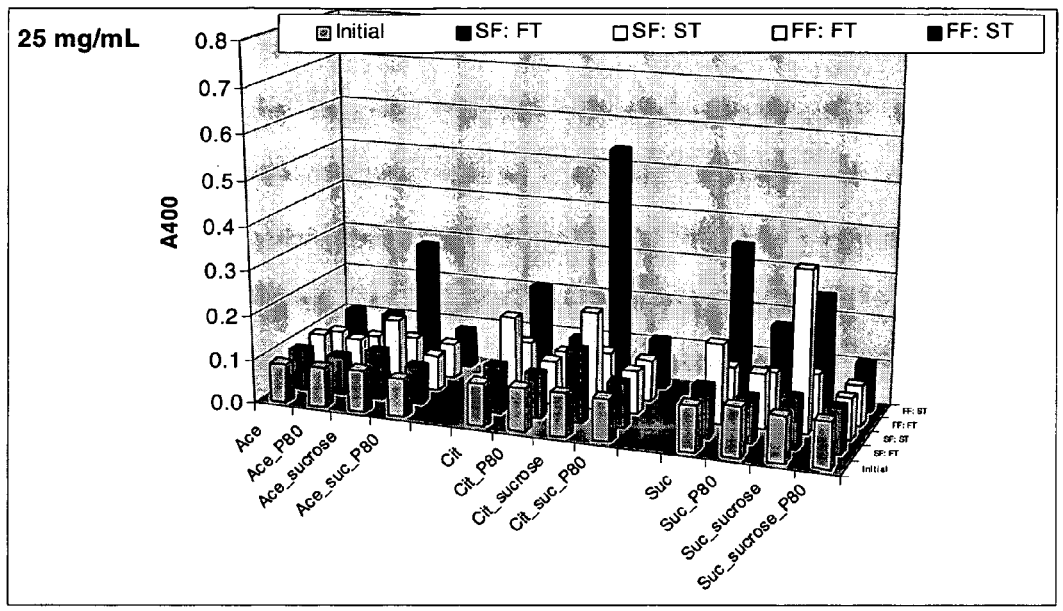
FIG. 30A is a bar graph depicting the $A_{400}$ of anti-5T4 at 25 mg/ml in formulations containing various buffers (pH 5.5) and with or without polysorbate 80 (P80), and with or without sucrose under different freezing and thawing regimens. FF is fast freeze, SF is slow freeze, FT is fast thaw, and ST is slow thaw.
Figure 30B:
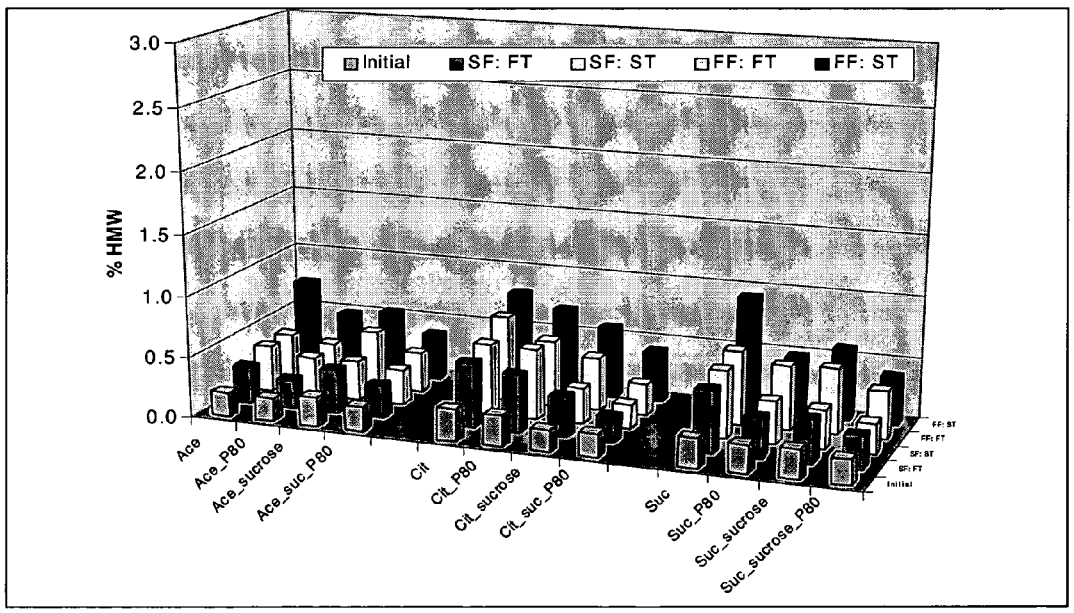
FIG. 30B is a bar graph depicting the percentage of high molecular weight (HMW) species of anti-5T4 at 25 mg/ml in formulations containing various buffers (pH 5.5) and with or without polysorbate 80 (P80), and with or without sucrose under different freezing and thawing regimens. FF is fast freeze, SF is slow freeze, FT is fast thaw, and ST is slow thaw.

Turbidity and percentage of high molecular weight species were also assayed after multiple (ten) freeze/thaw cycle using samples with a protein (anti-5T4) concentration of 25 mg/ml. (FIG. 30A and FIG. 30B). These data demonstrated that the anti-ST4 is not sensitive to freeze/thaw stress at a concentration of 25 mg/ml. There was only a slight decrease in turbidity and the percentage of high molecular weight species with the addition of polysorbate 80 and/or sucrose after ten freeze/thaw cycles. The turbidity results also demonstrate that there was no benefit, and in some cases it was detrimental, to anti-5T4 stability when sucrose was added to a formulation. Use of acetate buffer in a formulation resulted in slightly lower in turbidity and a lower percentage of high molecular weight species under most of freeze/thaw conditions.

Figure 31A:
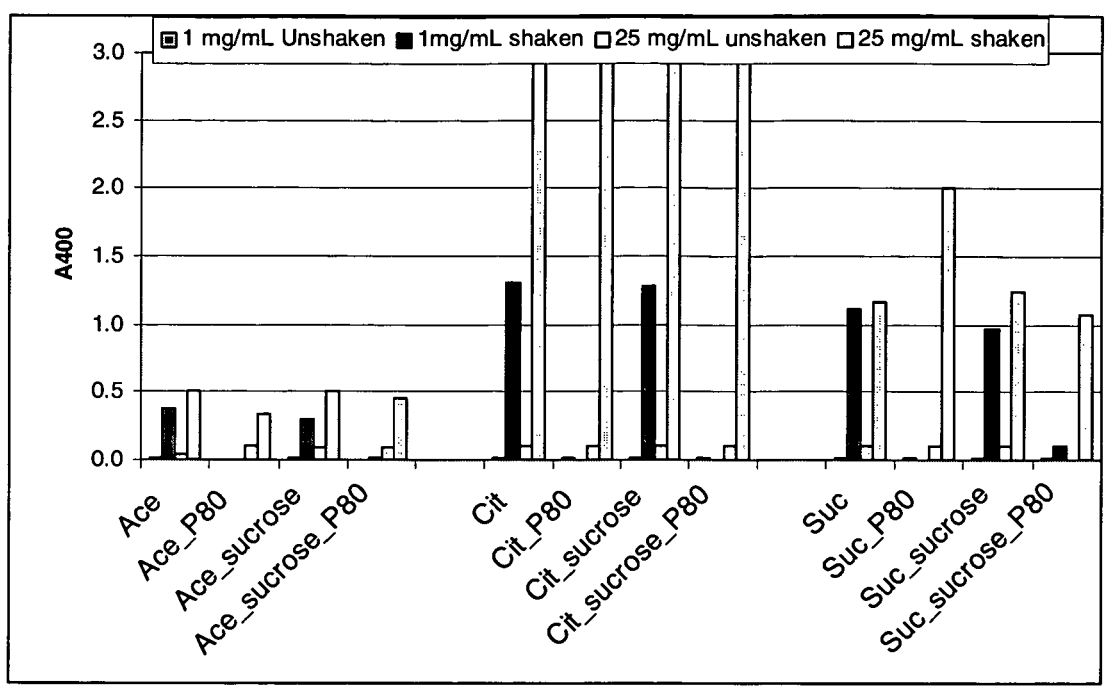
FIG. 31A is a bar graph depicting the $A_{400}$ of anti-5T4 at 1 mg/ml or 25 mg/ml in various formulations with or without polysorbate 80 (P80) and with or without sucrose. Samples were shaken or unshaken. "*" Indicates that turbidity exceeds the upper limit of the instrument.
Figure 31B:
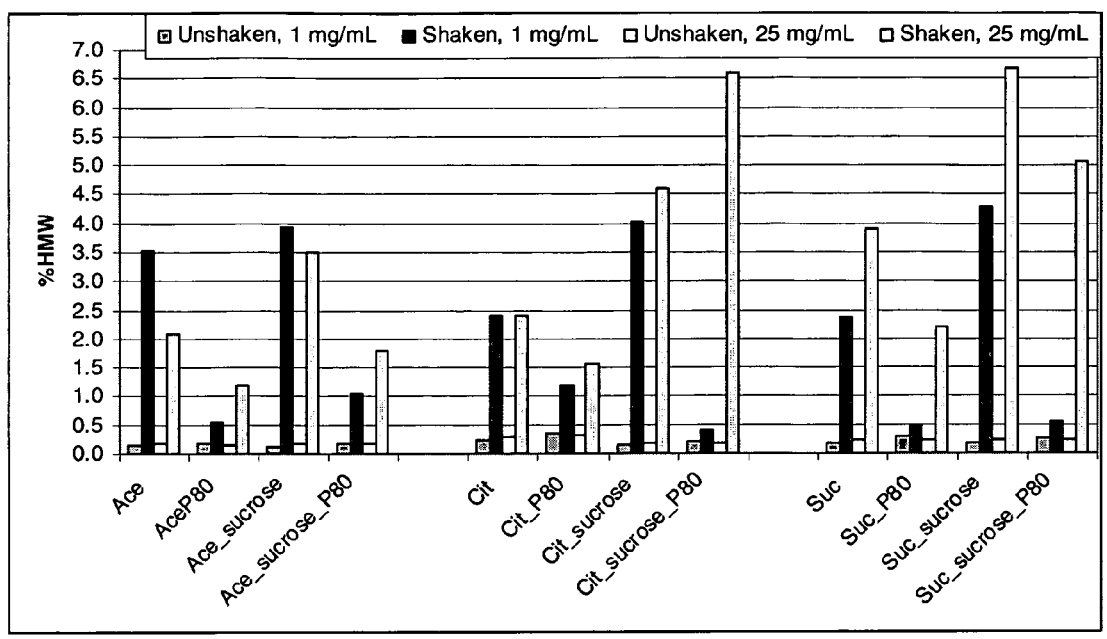
FIG. 31B is a bar graph depicting the percentage of high molecular weight species (HMW) of anti-5T4 at 1 mg/ml or 25 mg/ml in various formulations with or without polysorbate80 (P80) and with or without sucrose. Samples were shaken or unshaken.

Stability under conditions of shaking were assayed by measuring turbidity ($A_{400}$) and percentage of high molecular weight species using formulations containing 25 mg/ml anti-5T4. FIG. 31A and FIG. 31B illustrate the results of turbidity measurements of samples in various formulations. These data demonstrate that anti-5T4 is very sensitive to shaking stress in when in a formulation containing citrate buffer. There was a decrease in turbidity and the percentage of high molecular weight species some formulations with the addition of polysorbate 80 with both 1 mg/ml and 25 mg/ml samples, but there is no benefit to adding sucrose to formulations. Acetate buffer formulations generally exhibited the lowest turbidity.

Surfactant and Cryoprotectant

Some of the experiments described supra (e.g., those illustrated in FIG. 29A, FIG. 29B, FIG. 30A, FIG. 30B, FIG. 31A, and FIG. 31B) include data in which the formulation included a surfactant (polysorbate 80) and/or a cryoprotectant (sucrose). With respect to stability after freezing, samples containing 25 mg/ml anti-5T4 were not sensitive to freeze/thaw stress. Anti-5T4 was stable under slow freezing conditions regardless of protein concentration or thaw condition.

Polysorbate 80 was not necessary to improve stability of the 25 mg/ml protein concentration samples when a fast thaw protocol was applied.

The addition of sucrose to a formulation did not improve stability for those samples containing at 25 mg/ml anti-5T4. For samples containing 1 mg/ml, polysorbate 80 and sucrose protected the anti-5T4 during freeze/thaw, particularly under fast freezing conditions (FIG. 29A and FIG. 29B and FIG. 30A and FIG. 30B).

The stability of anti-5T4 in various formulations under shaking conditions was also examined. Polysorbate 80 contributed to the minimization of turbidity and minimization of the percentage high molecular weight species of anti-5T4 formulations at a protein concentration of 25 mg/ml when the protein is shaken at extremely high rpm. In formulations containing 1 mg/ml anti-5T4, polysorbate 80 protected the protein against agitation stress (FIG. 31A and FIG. 31B).

These data demonstrate that for higher protein concentrations (e.g., 25 mg/ml), anti-5T4 is stable under freeze/thaw stress. There was little or no benefit to adding surfactant to a formulation under most freeze/thaw conditions, particularly in formulations containing acetate buffer. Furthermore, there is no need to use a cryoprotectant (e.g., sucrose) in the formulations. Polysorbate 80 was useful for stabilizing anti-5T4 under conditions of severe agitation.

In addition, it was found that samples containing low protein concentrations (e.g., 1 mg/mi anti-5T4) were stable under slow freezing conditions. In such low protein samples, polysorbate 80 and sucrose protected the protein (anti-5T4) against freeze/thaw-induced denaturation. Also, in the low protein concentration samples, polysorbate 80 protected the protein against agitation-induced denaturation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A formulation comprising
   (a) an isolated polypeptide, wherein the polypeptide is an anti-CD22 antibody; and (b) an aqueous solution having pH 4.0 to pH 8.0, wherein the formulation does not contain a cryoprotectant or surfactant, provided that the anti-CD22 antibody is present at a concentration of about 10 to about 30 mg/mL, and the formulation comprises a buffer concentration of about 1 mM to about 100 mM.

2. The formulation of claim 1, wherein the buffer is an acetate buffer, HEPES, succinate buffer, phosphate buffer, citrate buffer, or combinations thereof.

3. The formulation of claim 1, wherein the anti-CD22 antibody has a pI of at least 6.0, 7.0, or 8.0.

4. The formulation of claim 1, wherein the pH of the formulation is about pH 5.0 to about pH 6.0.

5. The formulation of claim 1, wherein the pH of the formulation is about pH 5.0 to about pH 6.0 and the formulation is stored at about −80° C. to 0° C.

6. The formulation of claim 1, wherein the aqueous solution is about 20mM succinate, pH 6.0.

7. The formulation of claim 1, wherein the protein is an anti-Lewis Y antibody and the aqueous solution is about 10 mM Na citrate, pH 5.5 and about 75 mM NaCl.

8. The formulation of claim 1, wherein the protein is an anti-5T4antibody and the aqueous solution is about 10 mM Na acetate, pH 5.5.

9. The formulation of claim 1, wherein stability is determined by assaying at least one of (i) the percentage of high molecular weight species, (ii) the percentage of low molecular weight species, or (iii) the percentage of acidic species of the polypeptide compared to a control.

10. The formulation of claim 1, wherein the anti-CD22 antibody is purified at least 95%.

11. The formulation of claim 1, wherein the formulation is sterile.

12. A method of conjugating a polypeptide to a second agent, the method comprising.
   (a) obtaining a polypeptide from the formulation of claim 1, and
   (b) conjugating the polypeptide to the second agent.

13. The method of claim 12, wherein the polypeptide is an antibody.

14. The method of claim 12, wherein the second agent is a toxin.

15. A conjugated polypeptide produced by the method of claim 12.

16. The formulation of claim 1, wherein the anti-CD22 antibody is stable at frozen stage for at least 3 weeks at about −80° C. to 0° C.

17. The formulation of claim 1, wherein not more than 0.5% of the polypeptide is a high molecular weight species.

* * * * *